(12) United States Patent
Burkinshaw et al.

(10) Patent No.: US 6,290,704 B1
(45) Date of Patent: Sep. 18, 2001

(54) APPARATUS AND METHOD FOR ANTERIOR AND POSTERIOR REFERENCED SIZING AND DISTAL FEMUR RESECTION

(75) Inventors: Brian D. Burkinshaw; Donald W. Dye, both of Pflugerville, TX (US)

(73) Assignee: Sulzer Orthopedics Inc., Austin, TX (US)

( * ) Notice: Subject to any disclaimer, the term of this patent is extended or adjusted under 35 U.S.C. 154(b) by 0 days.

(21) Appl. No.: 09/392,600

(22) Filed: Sep. 9, 1999

Related U.S. Application Data

(63) Continuation-in-part of application No. 09/149,989, filed on Sep. 9, 1998, now Pat. No. 6,013,081.

(51) Int. Cl.[7] ................................................. A61B 17/15
(52) U.S. Cl. ........................ 606/88; 606/96; 606/102
(58) Field of Search ........................... 606/79, 82, 86, 606/87, 88, 89, 96, 102

(56) References Cited

U.S. PATENT DOCUMENTS

| | | |
|---|---|---|
| 4,703,751 | 11/1987 | Pohl . |
| 5,364,401 * | 11/1994 | Ferrante et al. ................... 606/84 |
| 5,417,694 | 5/1995 | Marik et al. ...................... 606/88 |
| 5,486,178 | 1/1996 | Hodge ................................ 606/82 |
| 5,562,675 | 10/1996 | McNulty et al. ................. 606/96 |
| 5,569,261 | 10/1996 | Marik et al. ...................... 606/88 |
| 5,624,444 | 4/1997 | Wixon et al. ..................... 606/88 |
| 5,662,656 | 9/1997 | White ................................ 606/88 |
| 5,688,279 | 11/1997 | McNulty et al. ................. 606/88 |
| 5,688,281 | 11/1997 | Cripe et al. ....................... 606/88 |

FOREIGN PATENT DOCUMENTS

| | | |
|---|---|---|
| 0 340 176 A2 | 11/1989 | (EP) . |
| 0 380 451 A2 | 8/1990 | (EP) . |
| WO 97/30640 | 8/1997 | (WO) . |

OTHER PUBLICATIONS

Informational Brochure: Wallaby, Leaps Ahead in Knee Joints, Protek, Jan. 1994.

Informational Brochure: Osteonics, Palm Beach Instruments, Surgical Protocol, Undated.

* cited by examiner

Primary Examiner—David O. Reip
(74) Attorney, Agent, or Firm—Philip S. Lyren

(57) ABSTRACT

Apparatus for distal femur sizing and resection includes a sizer member and a platform pivotably connected to the sizer member. An anterior femoral cut guide is movably engaged with the sizer member and includes a first retainer for retaining a removable reference device for referencing, and a second retainer for retaining a removable distal cut guide subsequent to removal of the reference device to position the distal cut guide on the femur. Retaining guides extend from the femoral cut guide. A slide member is movably mounted on the retaining guides. The slide member includes a carriage member, and a plunger resiliently mounted in the carriage, and movable for retaining the slide member on the retaining guides.

19 Claims, 21 Drawing Sheets

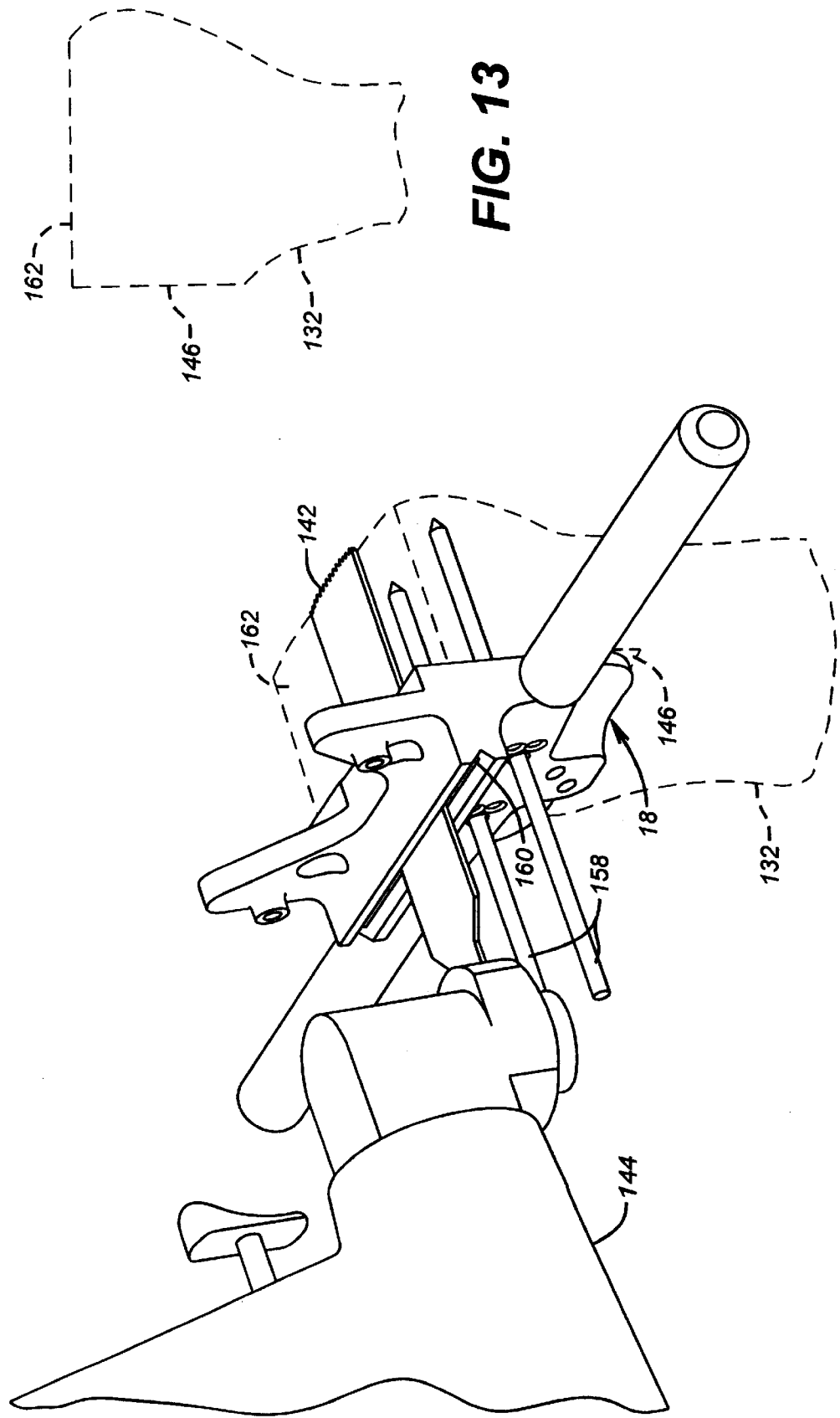

APPARATUS AND METHOD FOR ANTERIOR AND POSTERIOR REFERENCED SIZING AND DISTAL FEMUR RESECTION

This is a continuation-in-part of U.S. application Ser. No. 09/149,989, filed on Sep. 9, 1998, now U.S. Pat. No. 6,013,081.

BACKGROUND

The disclosures herein relate generally to orthopedic implant systems and more particularly to an anterior or posterior referencing instrument including an anterior femoral cutting guide and a distal femoral cutting guide.

There are many problems encountered by orthopedic surgeons when attempting to properly size and reset the distal femoral articulating surfaces in preparation for total knee arthroplasty. The intramedullary canal is located for proper centering of an intramedullary rod to be inserted therein. Anterior or posterior referencing are used to properly establish cutting planes for receiving a properly sized femoral reconstruction component. In anterior referencing, anterior-posterior placement of the femoral component is based on the anterior cortex as a primary point of reference. In posterior referencing, anterior-posterior placement of the femoral component is based on the posterior femoral condyles as a primary point of reference.

Numerous approaches have been taken to achieve accurate sizing for a knee prosthesis. U.S. Pat. No. 5,417,694 and U.S. Pat. No. 5,569,261, each disclose a distal femoral cutting instrument which includes an intramedullary rod for referencing the patient's intramedullary canal. A valgus block with a flat reference surface mounts to the intramedullary rod at a bore of the valgus block. The bore of the block has a slant with respect to the flat reference surface on the valgus block. The reference surface defines a line that is normal to the mechanical axis of the patient while the bore of the valgus block tracks the patient's biomechanical axis. A distal femoral cutting block removably attaches to the valgus block and provides a flat cutting guide surface for shaping the patient's distal femur. The valgus block, intramedullary rod, and a stylus are removed as a unit before shaping of the distal femur. An indexing system includes a gauge having a series of openings corresponding to "anterior" referencing and to "posterior" referencing. During anterior referencing, the gauge allows the surgeon to select the next smaller size prosthesis if the size falls in between available sizes. In posterior referencing, the gauge allows the surgeon to select the next larger size prosthesis if the gauge measures a size that falls in between available sizes.

In U.S. Pat. No. 5,486,178, a femoral preparation instrumentation system and method employs a multi-purpose sizing guide for placement at the distal femur, secured to an intramedullary alignment rod seated within the femur, enabling the determination of the appropriate size for the femoral knee prosthesis to be implanted and the setting of the axial rotational position of the femoral knee prosthesis, and providing for the accomplishment of preliminary posterior condylar cuts and the location of a distal femoral resection guide at the distal femur, while the sizing guide remains in place at the distal femur.

U.S. Pat. No. 5,624,444 discloses a set of instruments and method for use in knee replacement surgery, specifically to make the necessary femoral resections. The set of instruments allows the necessary femoral resections to be performed with fewer instruments, and with fewer necessary steps for the surgeon to take. The set of instruments includes a three-dimensional jig which references the anterior and posterior femoral condyles to allow determinations as to alignment, placement, and prosthesis size before any bone cuts are made.

U.S. Pat. No. 5,662,656 discloses instrumentation for and a method of sizing the end of a distal femur, and resecting the distal femur. An instrument body construct is provided with an instrument body and a valgus module for attachment to the instrument body. The instrument body construct has a distal aspect abutting surface with a planar face for abutting the distal aspect of a distal femur at a fixed angle to the longitudinal axis of the distal femur, a posterior aspect abutting surface with a planar face for abutting the posterior aspect of the distal femur, and a passageway therethrough. An anterior feeler gauge is provided for attachment to the instrument body construct and for contacting a portion of the anterior aspect of the distal femur to indicate the anterior-to-posterior size of the distal femur. A resection guide is provided for attachment to the instrument body construct for guiding a bone resection tool to resect the distal femur. The resection guide may have a first position for guiding the bone resection tool to perform an anterior femoral resection, and a second position for guiding the bone resection tool to perform a distal femoral resection.

In U.S. Pat. No. 5,688,279, an alignment guide for positioning a saw guide at a predetermined position on the distal femur is placed on the femur and receives an intramedullary rod inserted in the femur. The guide has an arm for coupling the saw guide block. The guide includes an intercondylar saddle that engages the intercondylar notch of the femur to align the saw guide at a predetermined position proximal to the intercondylar notch.

U.S. Pat. No. 5,688,281 discloses an intramedullary alignment guide and method for use thereof for accurately preparing and shaping the distal femur end surface to receive a knee prosthesis. The guide references the femur intramedullary canal to ensure that a distal femoral resector is properly positioned at a selected angle with respect to a patient's mechanical axis. The intramedullary alignment guide includes an opening for inserting an intramedullary rod therethrough and into the intramedullary canal of a patient. The guide includes an adjustment mechanism which allows a surgeon to quickly and easily deflect an attached distal femoral resector into a desired angular displacement with respect to the intramedullary canal. The distal femoral resector is angled with respect to the intramedullary canal so that a cut can be made in a patient's distal femur end which is perpendicular with the patient's mechanical axis. The guide can be used on patients having various anatomies, and in operations involving both the right and left legs. A slighting tool is also disclosed which allows a surgeon to externally verify that the distal femoral resector is properly aligned with the patient's mechanical axis.

Therefore, what is needed is an instrument which permits anterior and posterior referenced sizing and guide slots for making both the anterior reference femoral cut and the distal femoral cut thus providing a first and a second locating datum for subsequent use of a chamfer speed block.

SUMMARY

One embodiment, accordingly, provides an instrument which provides distal femoral sizing for a femoral prosthesis, and guides the cutting of the anterior and the distal femoral reference cuts. To this end, an apparatus for distal femur sizing and resection includes a sizer member. A femoral cut guide is movably engaged with the sizer member. Retaining guides extend from the femoral cut guide, and a slide member movably mounted on the retaining guides. A first member and a second member are sequentially removably attachable to the femoral cut guide. The first member is a reference device attached to the femoral cut guide for referencing, and the second member is a distal cut guide attachable to the femoral cut guide subsequent to removal of the reference device, to position the distal cut guide on the femur.

A principal advantage of this embodiment is that the device and technique consolidate several time consuming steps into a compact procedure utilizing a multi-purpose instrument, to accurately locate and make the anterior femoral reference cut and the distal femoral reference cut.

BRIEF DESCRIPTION OF THE DRAWINGS

FIG. 12 is an isometric view illustrating another reference cut being made using an embodiment of a portion of the device engaged with the distal femur.

FIG. 13 is a side view of the distal femur including the completed reference cuts.

DETAILED DESCRIPTION

Figure 1:
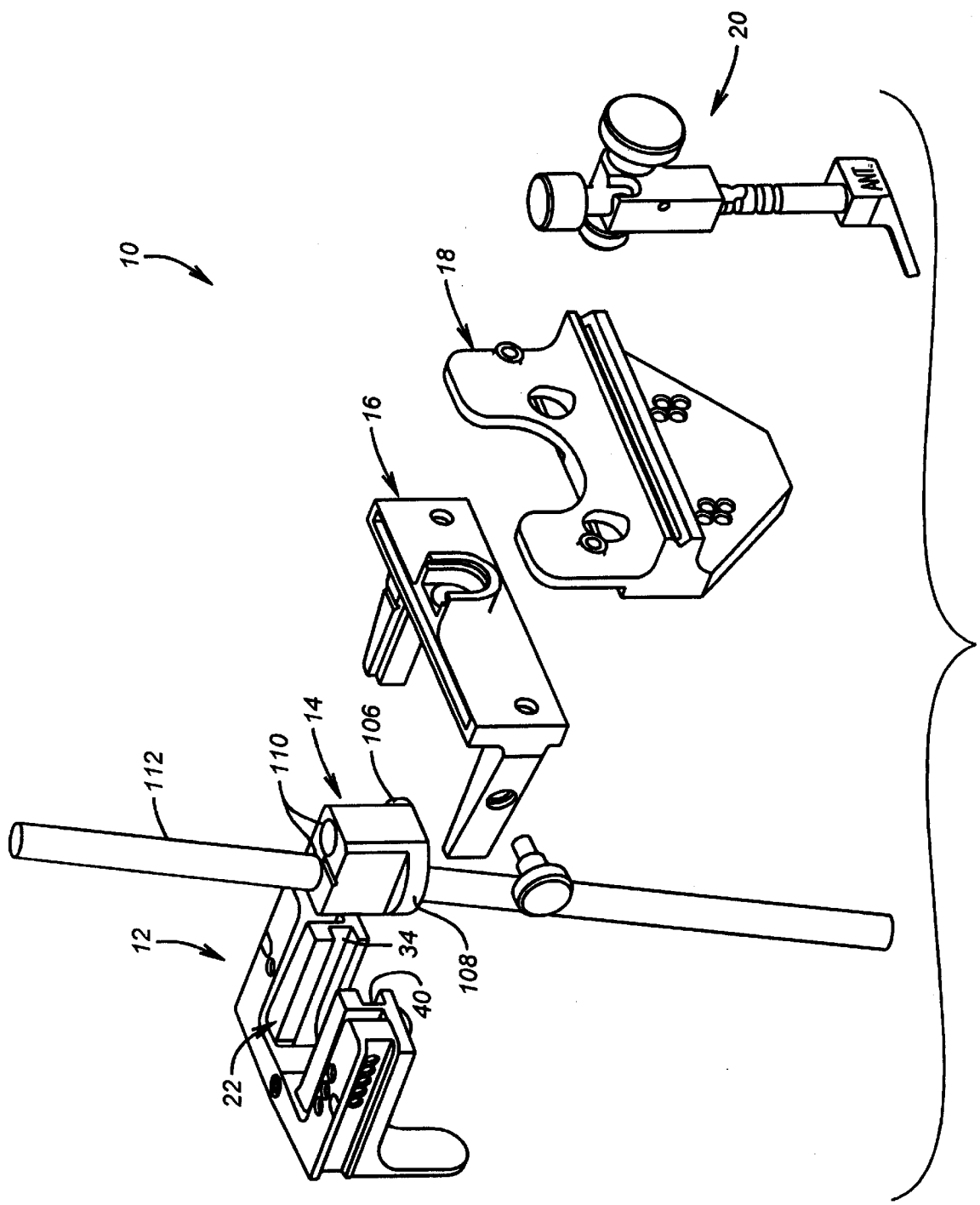
FIG. 1 is an exploded isometric view illustrating an embodiment of a distal femur sizing and resecting device.
Figure 2:
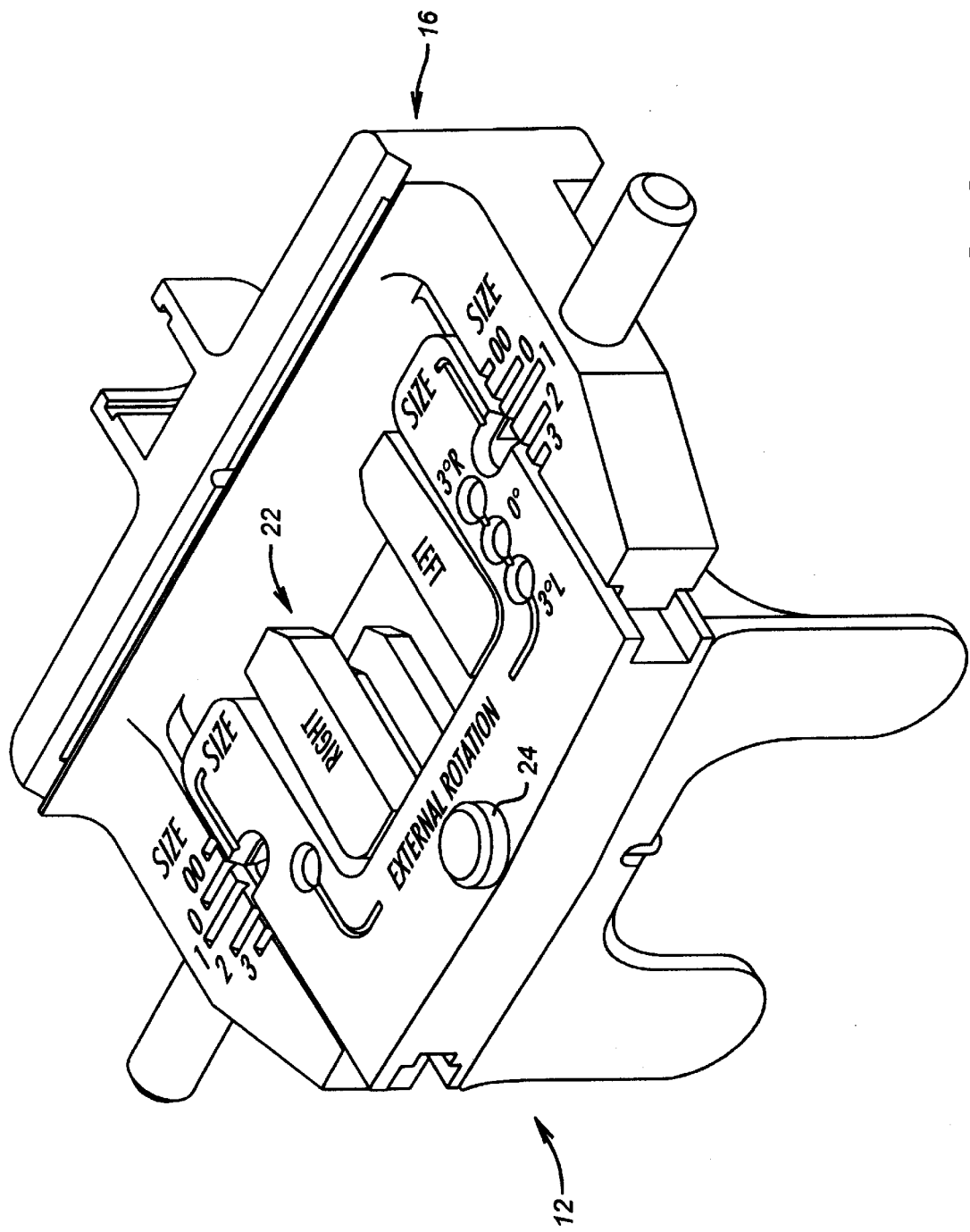
FIG. 2 is an isometric view illustrating an embodiment of assembled portions of the device.

A device for distal femur sizing and resection is generally designated 10 in FIG. 1, and includes a sizer member 12, a slide member, referred to as a slide stone 14, an anterior femoral cut guide 16, a distal cut guide 18, and a reference device 20. Sizer member 12, FIG. 2, includes a slide member receiver 22, connected to sizer member 12 at a pivot point 24 to permit slide member receiver 22 to pivot relative to sizer member 12.

Figure 3:
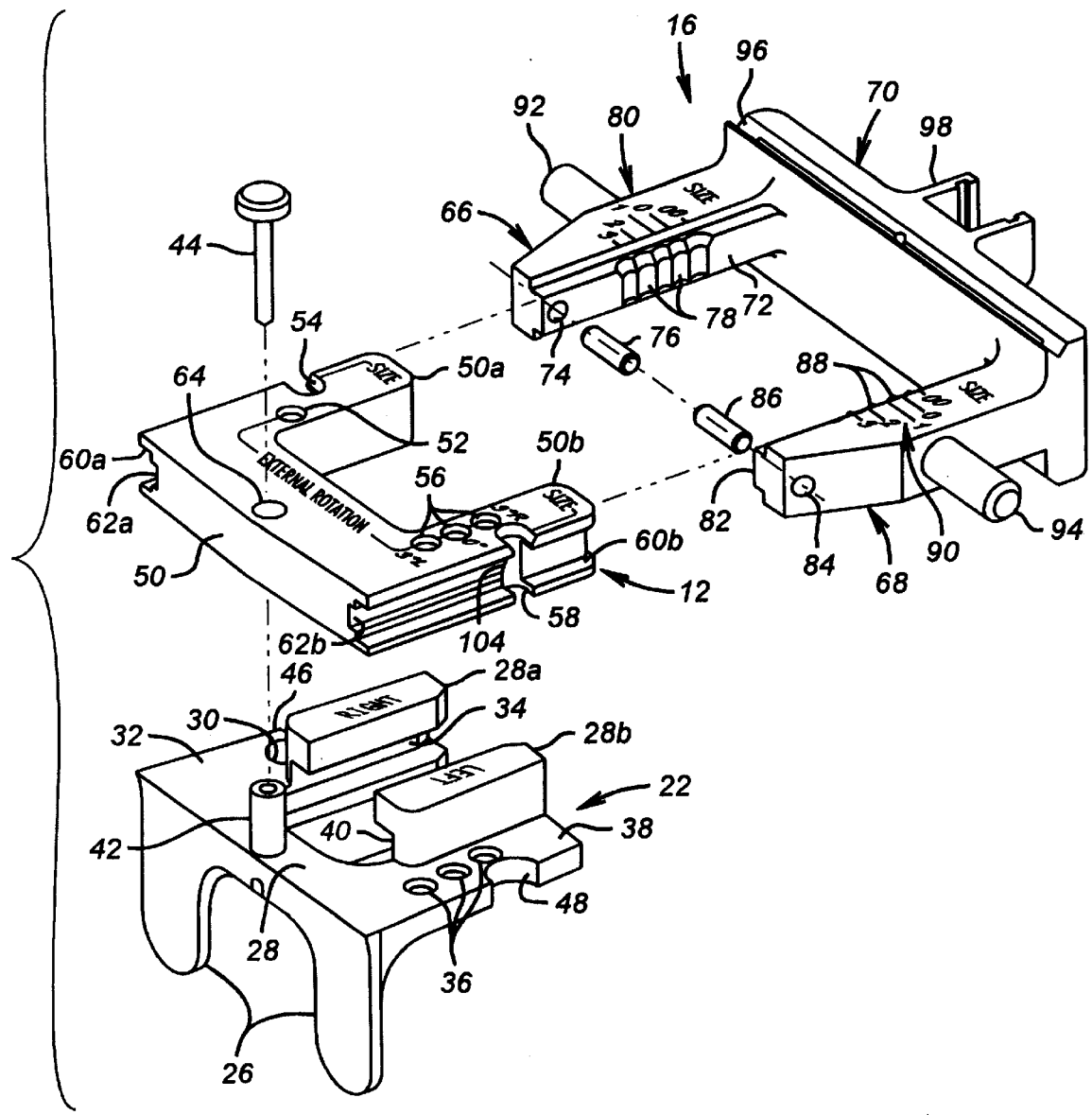
FIG. 3 is an exploded isometric view illustrating an embodiment of separated portions of the device.

Slide member receiver 22, FIG. 3, is generally L-shaped including a pair of paddles 26 and a bifurcated extension 28 including a first portion 28a and a second portion 28b. First portion 28a includes a rotation aperture 30 formed in a flange 32, and a slide member receiver groove 34. Second portion 28b includes a plurality of rotation apertures 36 formed in a flange 38, and a slide member receiver groove 40. A pivot pin receiver 42 extends from slide member receiver 22. Additionally, flange 32 includes a size scale notch 46 and flange 38 includes a size scale notch 48.

Sizer member 12 is generally U-shaped including a bifurcated portion 50 having a first portion 50a and a second portion 50b. First portion 50a includes a rotation aperture 52 and a size scale notch 54. Second portion 50b includes a plurality of rotation apertures 56 and a size scale notch 58. Sizer member 12 also includes a pair of opposed external grooves 60a and 60b and a pair of opposed pin grooves 62a and 62b formed in external grooves 60a and 60b, respectively. A pivot pin 44 is insertable into an aperture 64 formed in sizer member 12.

Figure 4:
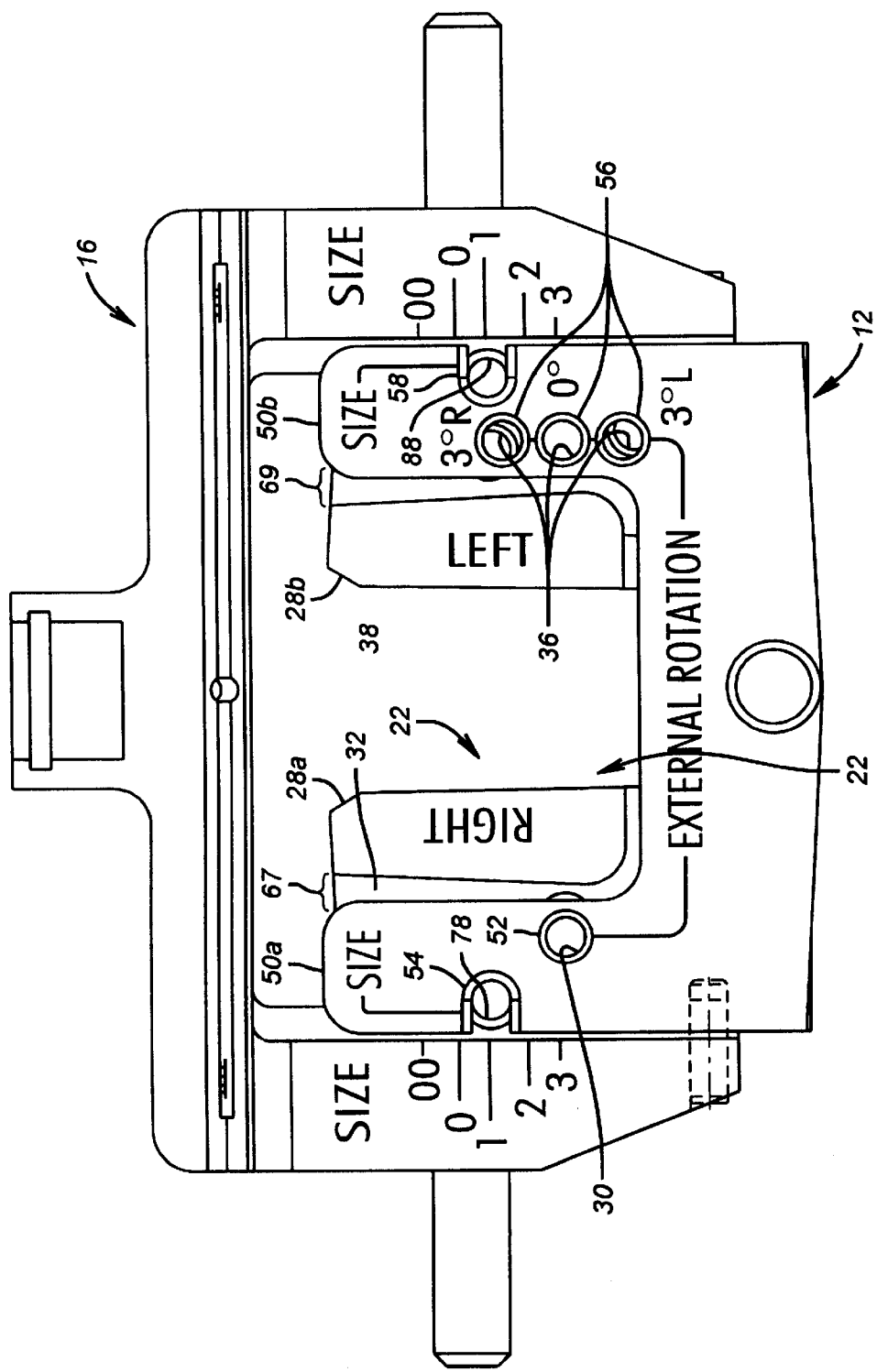
FIG. 4 is a top view illustrating an embodiment of assembled portions of the device.

When assembled, pivot pin receiver 42 extends through aperture 64 and receives pivot pin 44. First portion 28a, FIG. 4, and second portion 28b nest between first portion 50a and second portion 50b, respectively. A gap 67 between first portion 28a and 50a, and a gap 69 between second portion 28b and 50b, permits pivotal movement between sizer member 12 and slide member receiver 22. Also, such pivotal movement permits flange 32 to move relative to first portion 50a and simultaneously permits flange 38 to move relative to second portion 50b. This permits alignment between rotation apertures 30 and 52, and alignment between rotation apertures 36 and 56. Also, size scale notch 54, FIGS. 3 and 4, is aligned with size scale notch 46, and size scale notch 58 is aligned with size scale notch 48.

Figure 5:
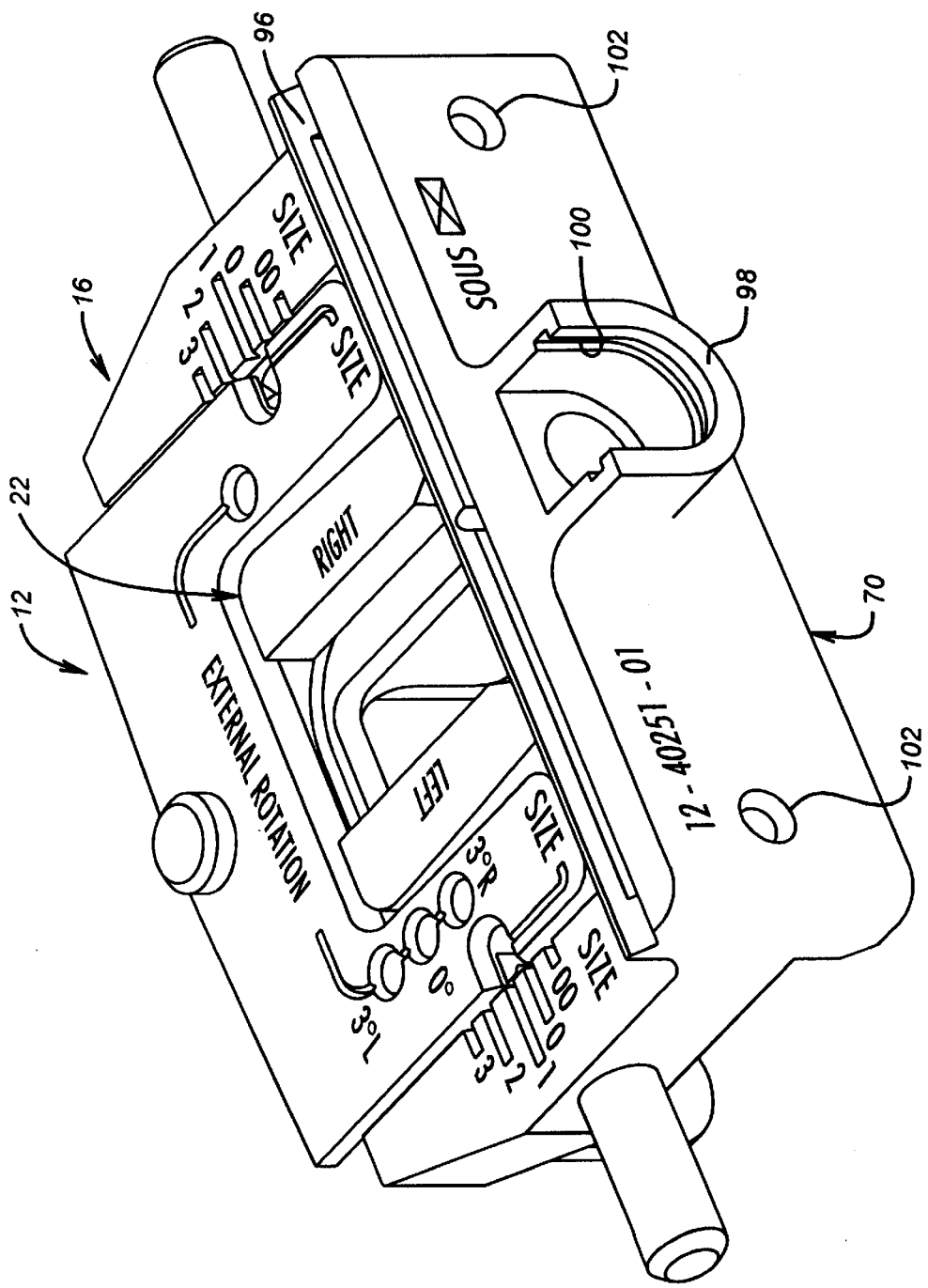
FIG. 5 is an isometric view illustrating an embodiment of assembled portions of the device.

Femoral cut guide 16, FIG. 3, is generally U-shaped including a first sizer extension 66, a second sizer extension 68 and a flange 70. First sizer extension 66 includes an internal tongue 72, an aperture 74 for receiving a pin 76 to protrude therefrom, a plurality of scalloped size scale notches 78, and a readable size index 80, including indices of 00, 0, 1, 2 and 3. Second sizer extension 68 includes an internal tongue 82, opposite tongue 72, an aperture 84 for receiving a pin 86 to protrude therefrom, a plurality of scalloped size scale notches 88, and a readable size index 90, including indices of 00, 0, 1, 2 and 3. Also, a pair of extensions 92 and 94 extend in opposite directions from extensions 66 and 68, respectively. Flange 70 includes a femoral cut guide slot 96, see also FIG. 5, a first femoral receiver 98 including a groove 100 formed therein, and a second femoral receiver including a pair of femoral temporary pin apertures 102. When assembled, FIG. 3, tongues 72 and 82 slide within grooves 60*a* and 60*b*, respectively. Pins 76 and 86 slide within grooves 62*a* and 62*b*, respectively, and capture sizer member 12 for limited sliding motion with femoral cut guide 16 by means of a stop 104, only one of which is visible in FIG. 3.

Figure 6:
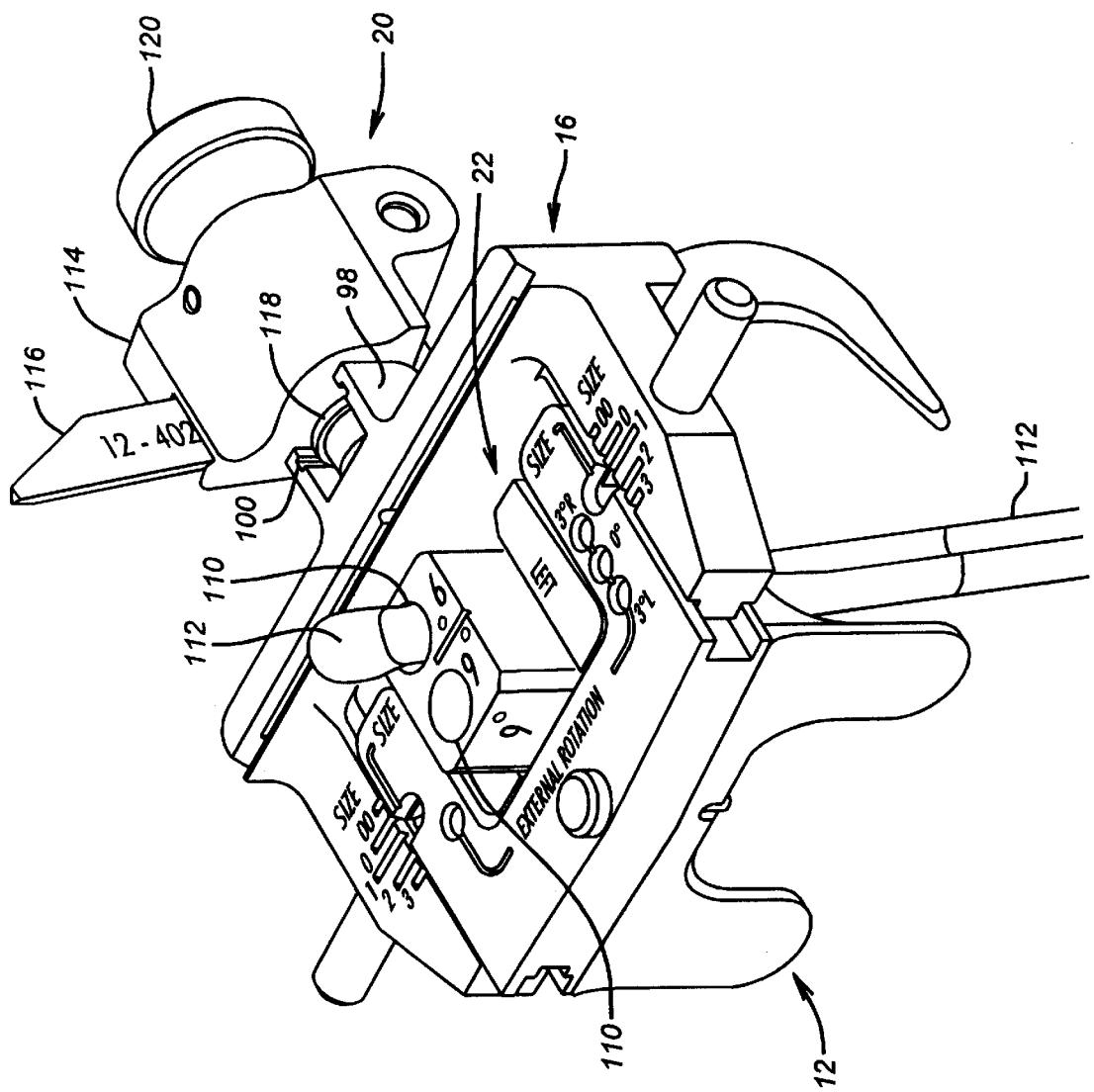
FIG. 6 is an isometric view illustrating an embodiment of assembled portions of the device.

Slide stone 14, FIG. 1, is slidably received by slide member receiver 22 due to engagement of a pair of opposed tongues 106 and 108 on slide stone 14, being slidably received in grooves 34 and 40, respectively. Also, slide member 14, includes a pair of angled apertures 110 formed therein for receiving an intramedullary rod 112, see also FIG. 6. Reference device 20 includes a stylus holder 114 and a posterior referencing stylus 116, FIGS. 6 and 7, adjustably mounted in stylus holder 114. A tongue portion 118, on stylus holder 114 is inserted in groove 100. Rotation of a threaded adjustable retainer 120 mounted in stylus holder 114, advances retainer 120 toward receiver 98, thus forcibly securing tongue 118 in groove 100. Adjustment of stylus 116, FIG. 7, in stylus holder 114, is accomplished by reciprocal movement of a resiliently mounted lock plunger 121 which engages one of several scalloped notches 122 formed in stylus 116, thus permitting stylus 116 to be moved within a slot 124 in stylus holder 114, in directions indicated by an arrow designated D1, so that a graduated size scale 126, on stylus 116, including indices 00, 0, 1, 2, 3, is movable relative to a size scale marker 128 on stylus holder 114.

Figure 7:
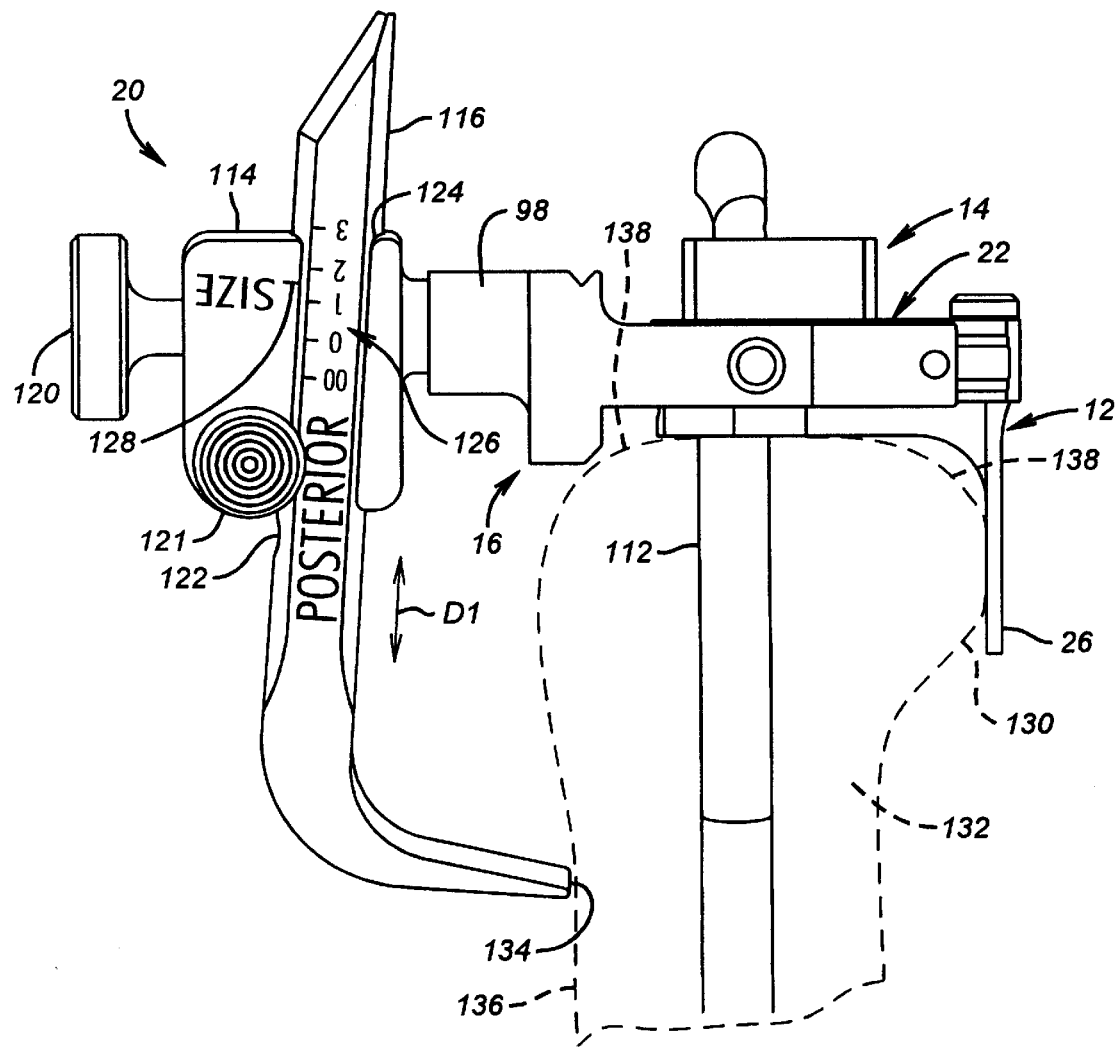
FIG. 7 is a side view illustrating an embodiment of assembled portions of the device engaged with a distal femur.
Figure 7A:
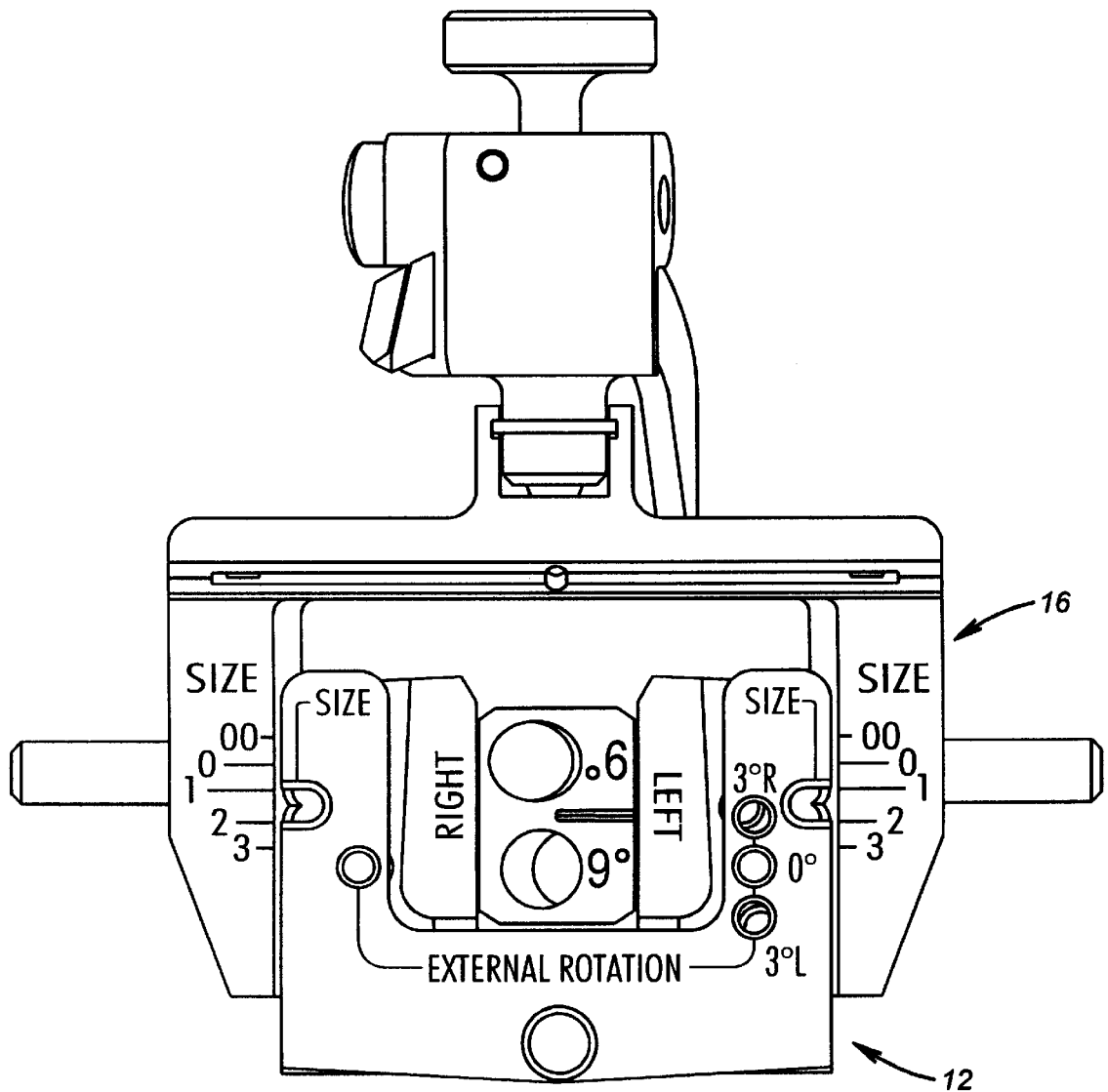
FIG. 7a is a plan view illustrating an embodiment of a sizer member and a femoral cut guide indicating a half size reading.

In the configuration generally illustrated in FIG. 7, paddles 26 engage posterior condyles 130 of a distal femur 132. A tip end 134 of stylus 116 is adjusted in the directions indicated by arrow D1 to engage anterior surface 136 of distal femur 132. A distal surface 138 of distal femur 132 abuts against slide member receiver 22. Intramedullary rod 112 is within the intramedullary canal of distal femur 132. Pivotal rotation of slide stone 14 with slide member receiver 22, sliding adjustment of sizer member 12 relative to femoral cut guide 16, and adjustment of stylus 116 in stylus holder 114, all done concurrently, will provide matched size readings on the reference device 20 and the sizer member 12, such that a prosthesis size is indicated. In the event that a half size reading is obtained, e.g. the reading is half way between the 1 and 2 indices on the stylus 116, as illustrated in FIG. 7, and on the femoral cut guide 16, FIG. 7*a*, an anterior reference stylus 116*a* may replace the posterior reference stylus 116, see FIG. 7*b*. The size of anterior reference stylus 116*a* is greater than the size of posterior reference stylus 116, i.e. the tip end 134*a* of stylus 116*a* has a longer extension than the tip end 134 of stylus 116. The difference in length is 1.5 mm which relates to one-half of an implant size. Therefore, an adjustment of stylus 116*a*, FIG. 7*b*, in directions indicated by arrow D1 will move tip 134*a* into engagement with anterior surface 136 of distal femur 132. This will result in a further concurrent sliding adjustment of sizer member 12 relative to femoral cut guide 16, and an adjusted matched size reading on the reference device 20 and the sizer member 12, such that a prosthesis size, e.g. size 1, is indicated on stylus 116*a*, and on the femoral cut guide 16, FIG. 7*c*. By switching to an anterior referencing stylus, the result is that more bone will be removed from the posterior condyles 130 when chamfer cuts are made in a subsequent procedure. The surgeon can adjust the distal cut, discussed below, to remove an equal amount of bone from the distal surface 138, to compensate for the bone removed from the posterior condyles 130. This results in balanced joint bone cuts.

Figure 8:
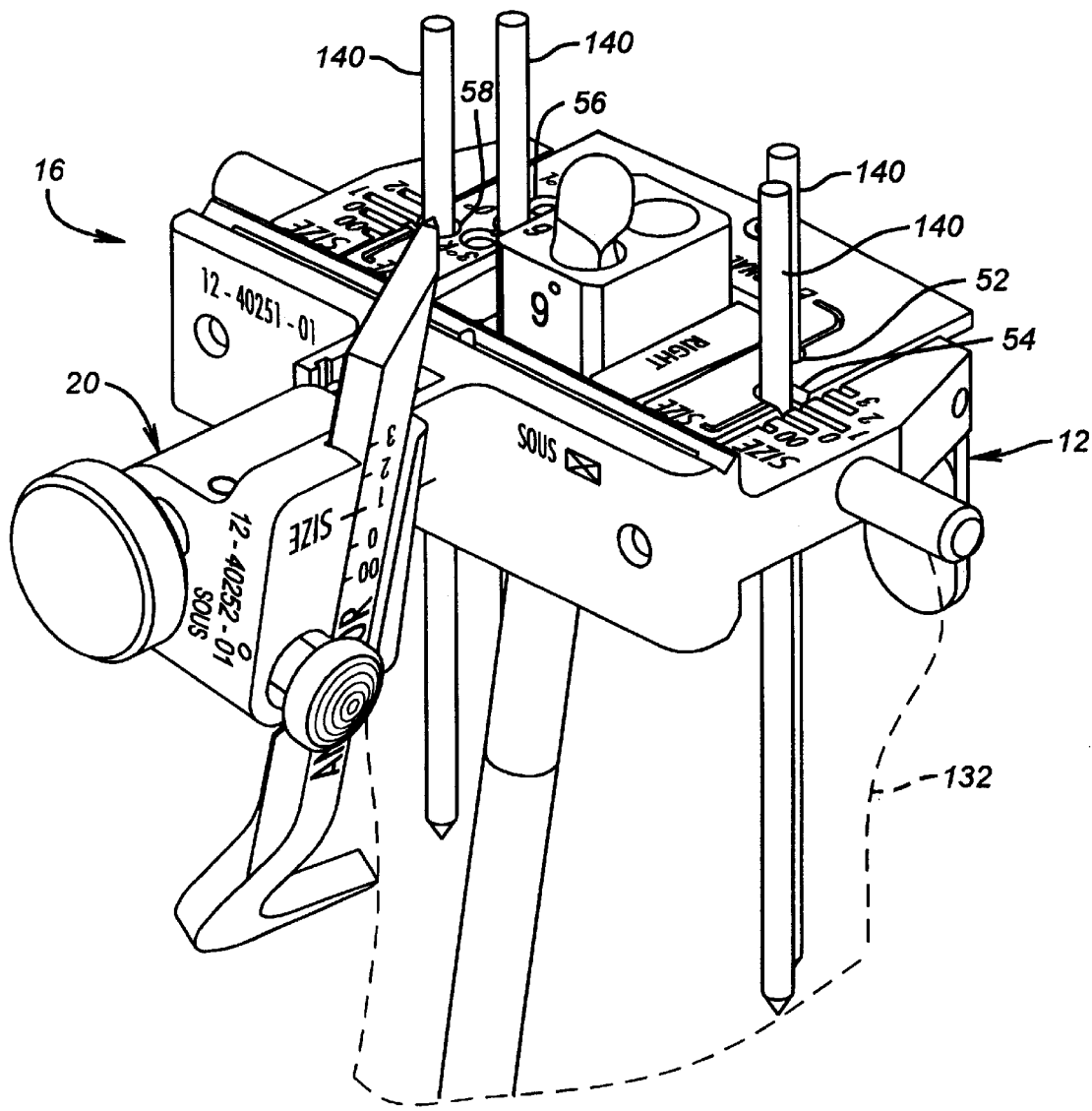
FIG. 8 is an isometric view illustrating an embodiment of assembled portions of the device engaged with the distal femur.
Figure 9:
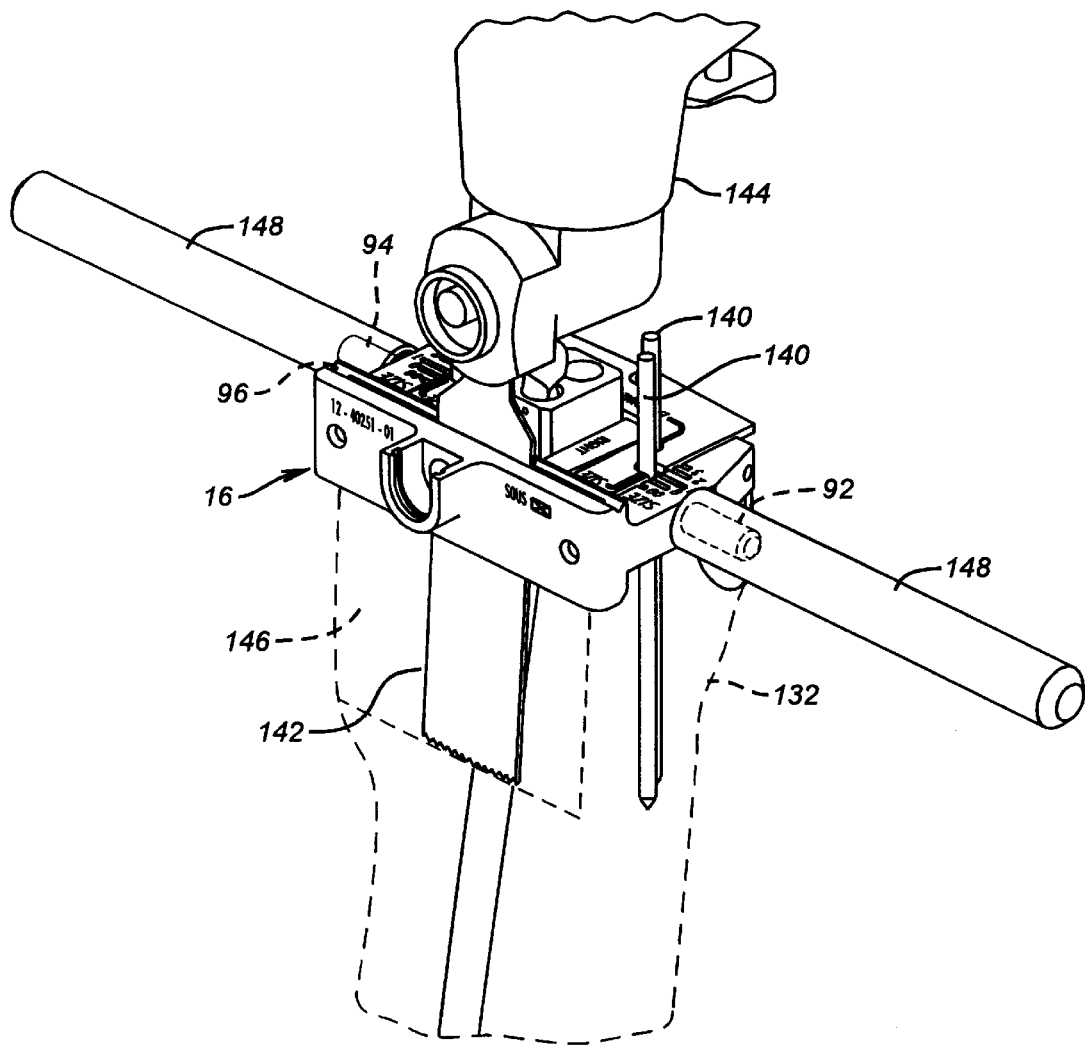
FIG. 9 is an isometric view illustrating a reference cut being made using an embodiment of assembled portions of the device engaged with the distal femur.

The readings on sizer member 12 may be retained by inserting pins 140 into distal femur 132, FIG. 8. Pins 140 insert through aligned ones of rotation apertures 56 and 36, FIGS. 3 and 4, rotation apertures 52 and 30 when aligned, aligned ones of size scale notches 54, 78 and 46 and aligned ones of size scale notches 58, 88 and 48 to create a macro lock. Thus, femoral cut guide 16 is secured to distal femur 132 and reference device 20 is removed, FIG. 9, to permit a saw blade 142 of a surgical cutting instrument 144 to be inserted through guide slot 96 to thus provide an anterior reference surface 146. Handles 148 are secured to extensions 92 and 94 to provide for hand-held stabilizing of femoral cut guide 16 during the cutting operation.

Figure 10:
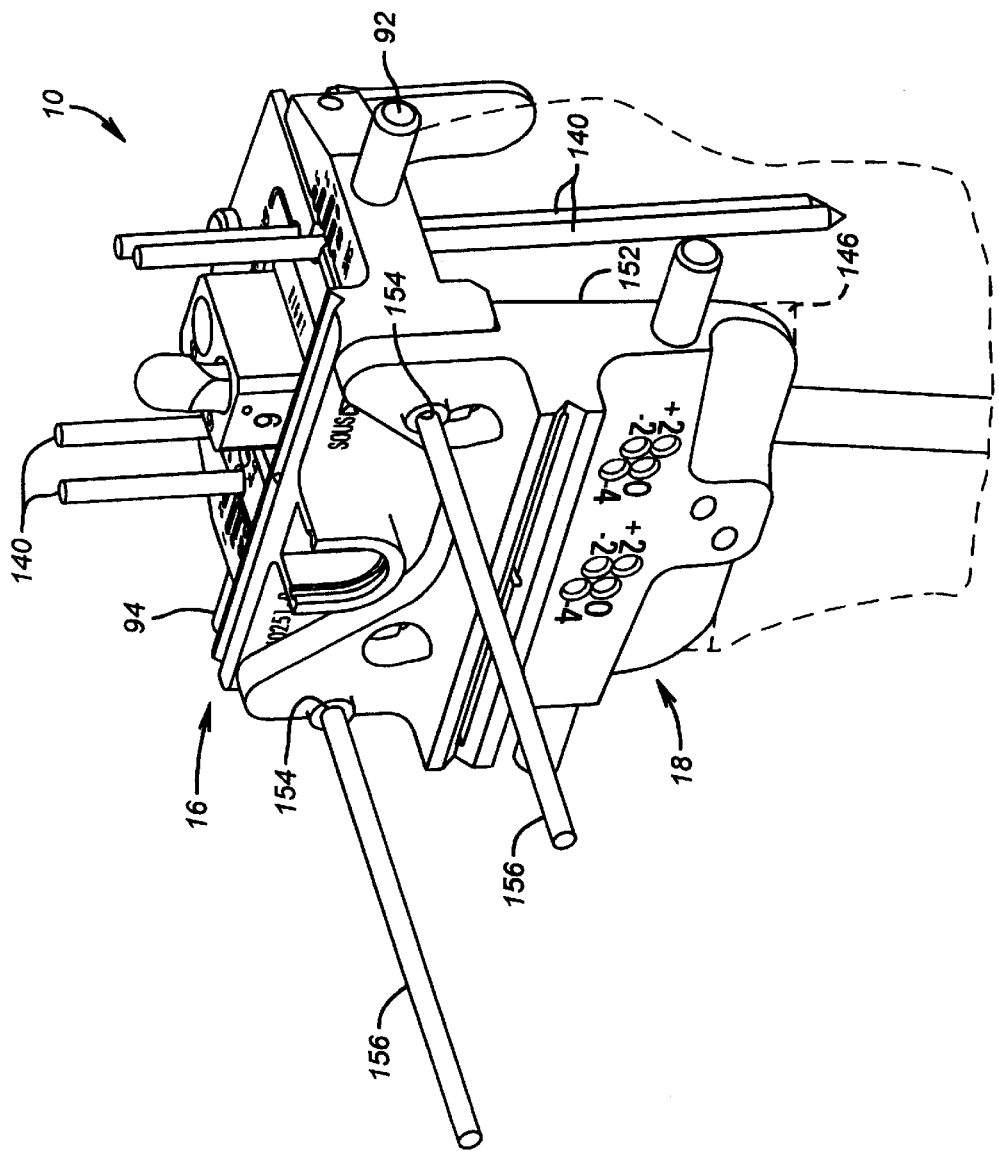
FIG. 10 is an isometric view illustrating an embodiment of assembled portions of the device engaged with the distal femur.
Figure 11:
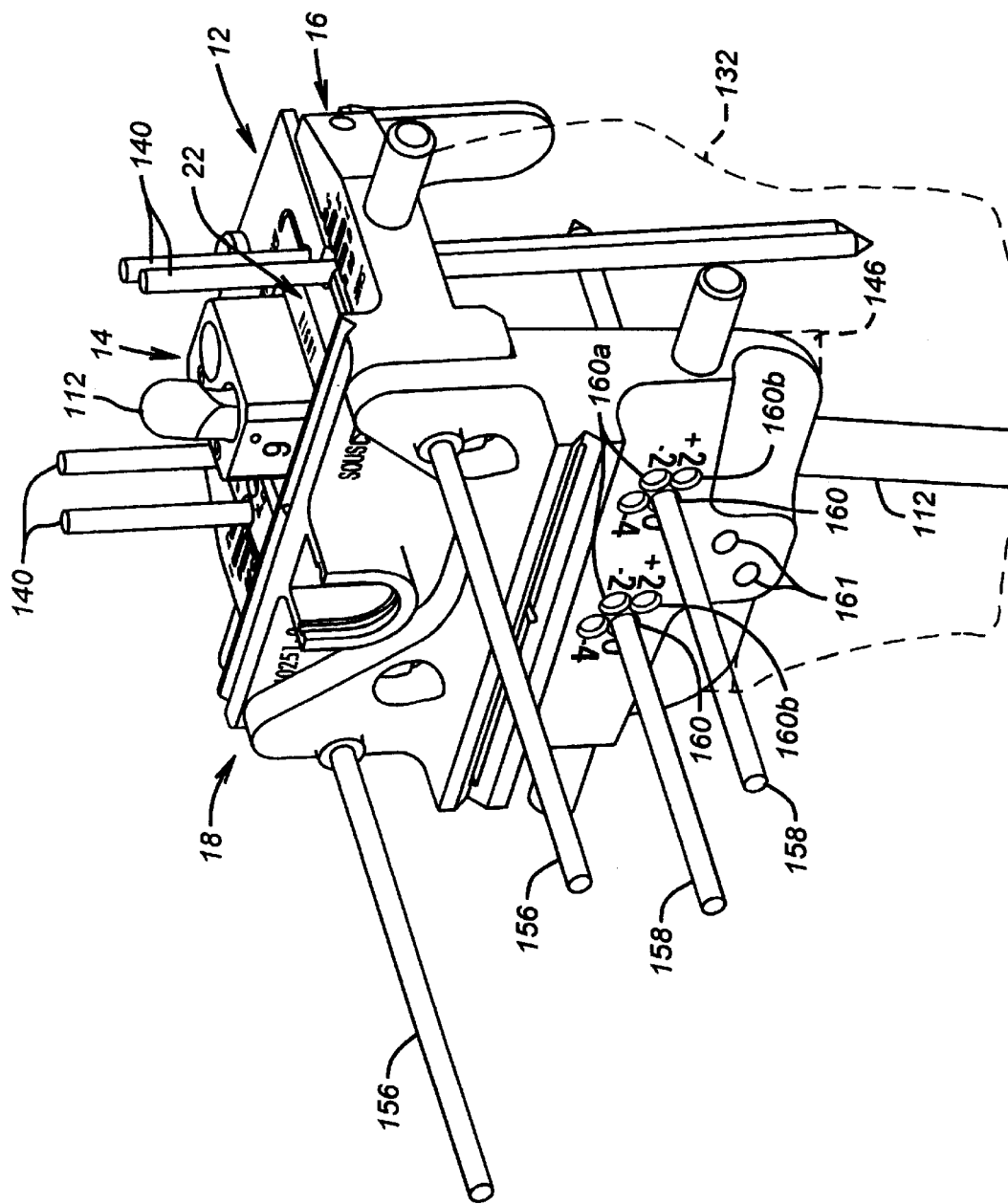
FIG. 11 is an isometric view illustrating an embodiment of assembled portions of the device engaged with the distal femur.

The device 10, FIG. 10, also provides for assisting in accurately locating and cutting a distal femoral surface. This is accomplished by first removing the handles 148 from extensions 92 and 94, and engaging the distal cut guide 18 with the femoral cut guide 16 and abutting a planar surface 152 of distal cut guide 18 with anterior reference surface 146. Also, distal cut guide 18 includes a pair of temporary pin apertures 154 which align with femoral temporary pin retaining apertures 102 (see also FIG. 5). A pair of temporary pins 156, inserted through aligned apertures 154 and 102, FIG. 10, temporarily retain distal cut guide 18 engaged with femoral cut guide 16. A plurality of distal attachment pins 158, FIG. 11, are inserted through a plurality of selected distal attachment pin apertures 160 in distal cut guide 18, and driven into distal femur 132 through the anterior reference surface 146, and temporary pins 156 are removed. It is at this point that the surgeon can make an adjustment to the distal cut, as mentioned above, to remove an equal amount of bone from distal surface 138, FIG. 7, to compensate for the bone to be removed from the posterior condyles 130, to provide the balanced joint bone cuts.

Figure 7B:
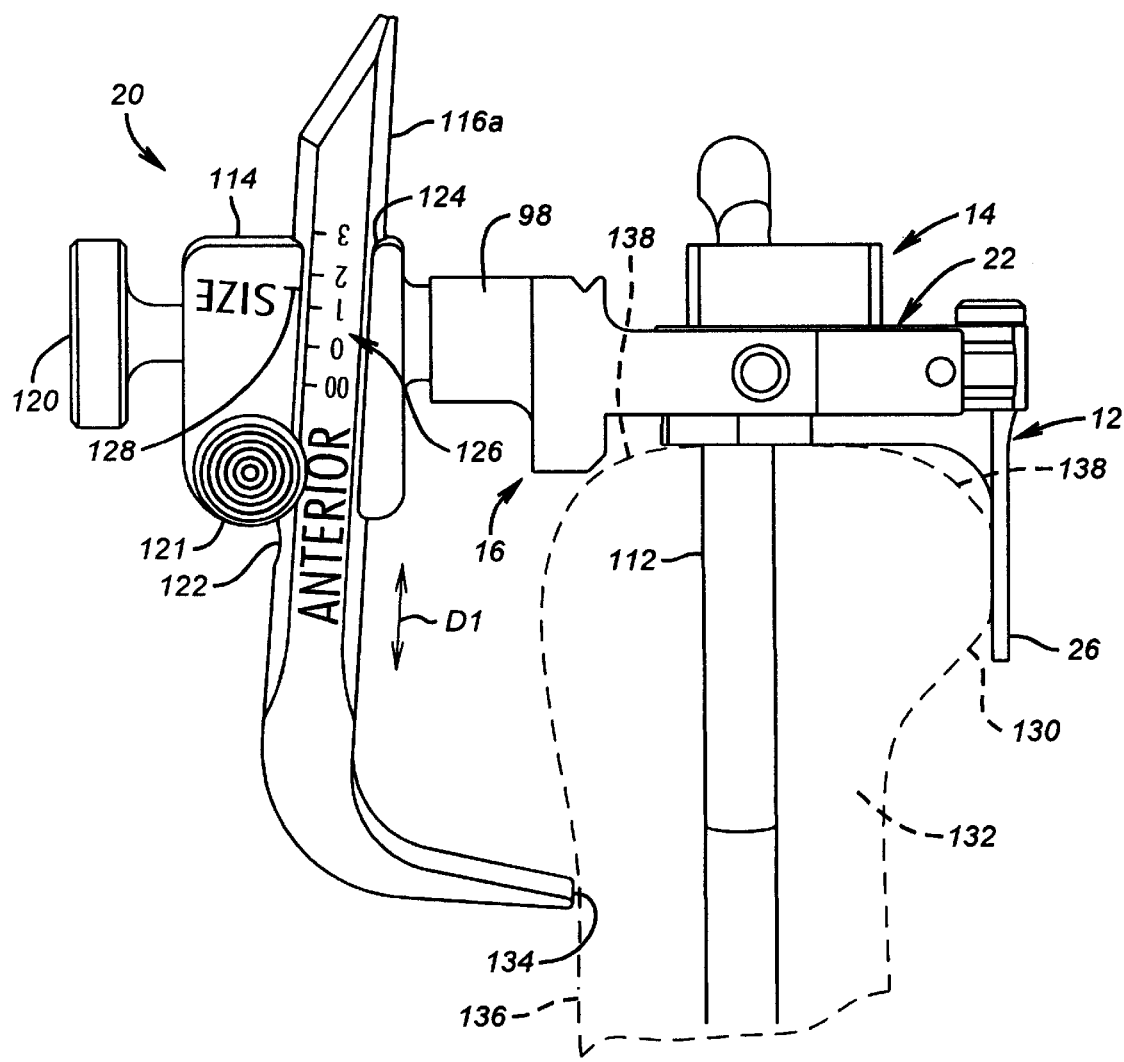
FIG. 7b is a side view illustrating an embodiment of assembled portions of the device engaged with the distal femur.
Figure 7C:
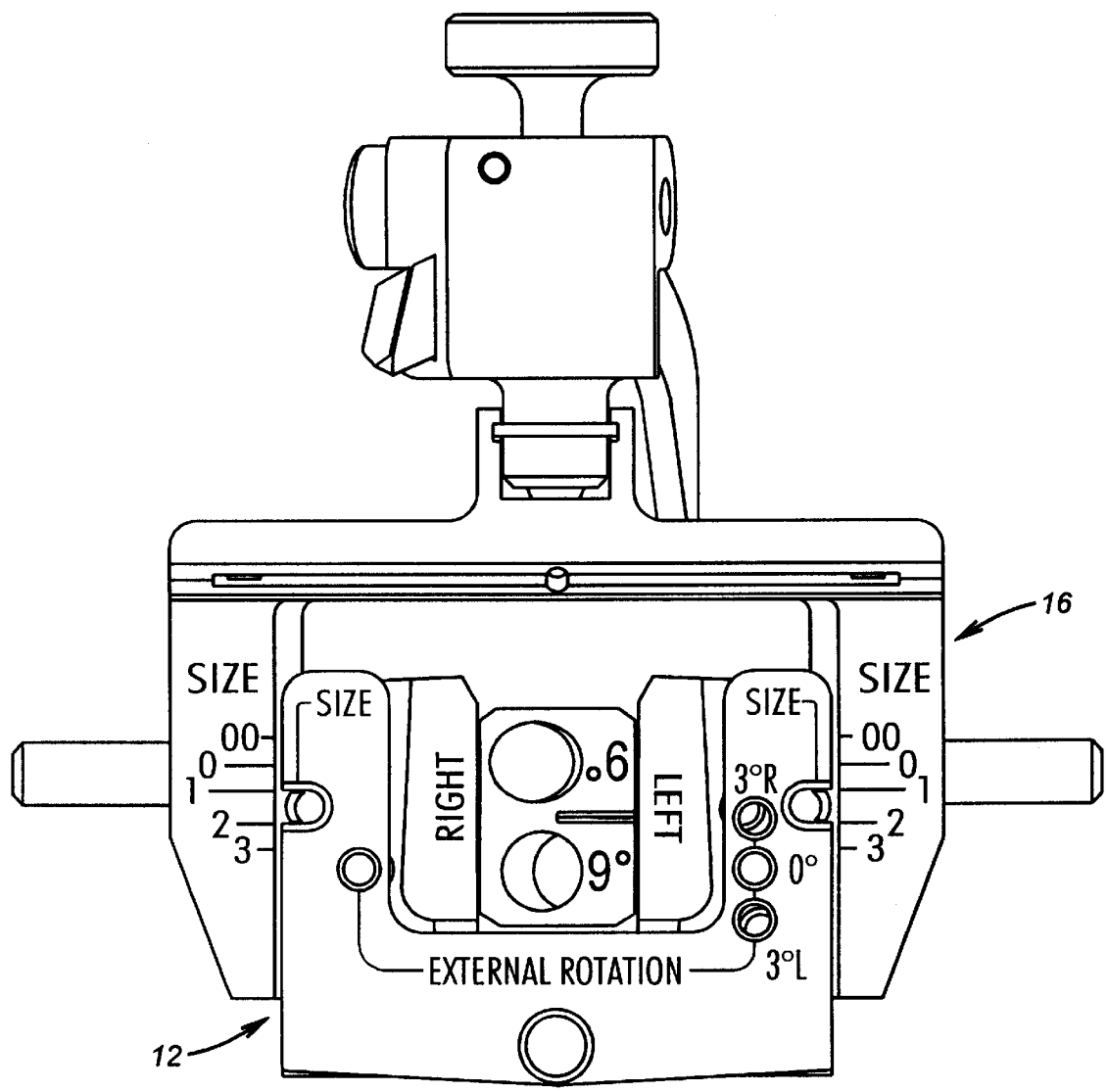
FIG. 7c is a plan view illustrating an embodiment of the sizer member and femoral cut guide indicating a prosthesis size of 1.

Routinely, the surgeon will insert attachment pins 158, FIGS. 11, 7 and 7*b,* through the O referencing pin apertures 160 to allow for a visual assessment of the amount of bone to be removed distally, to determine whether to adjust for the removal of more or less bone, the purpose being to balance the amount of bone removed, both distally and posteriorly from the femur, which will result in equal flexion and extension when the implant is positioned on the bone. For example, if the procedure began using the posterior referencing stylus 116, resulting in a half size reading, followed by a change to the anterior referencing stylus 116*a* as described above, the position of distal cut guide 18 may be adjusted downwardly to remove more bone distally. This is accomplished by sliding the distal cut guide 18 from the attachment pins 158, aligning pins 158 with a pair of −2 pin apertures 160*a,* and sliding distal cut guide 18 on pins 158 toward anterior reference surface 146. Alternatively, if the procedure began using the anterior referencing stylus 116*a,* followed by a change to the posterior referencing stylus 116, the position of distal cut guide 18 may be adjusted upwardly to remove less bone distally, by following the procedure above but aligning the pins 158 with a pair of +2 pin apertures 160*b.* If it is not necessary to change from one stylus to another, then pins 158 may remain in the O reference pin apertures 160. Additional pin apertures 161, are provided at an angle in distal cut guide 18, if it is desired to use additional attachment pins to create a macro lock.

Pins 140 along with femoral cut guide 16 are also removed including sizer member 12, slide receiver member 22, slide stone 14 and intramedullary rod 112. This results in distal cut guide 18, FIG. 12, remaining secured to the distal femur 132 by distal attachment pins 158. As a result, the saw blade 142 of the surgical cutting instrument 144 may be inserted through a distal cut guide slot 160 provided in distal cut guide 18, for making the distal femoral cut to establish a distal reference surface 162. Following the cutting operation, distal guide 18 is removed from distal femur 132 by removing distal attachment pins 158, resulting in the establishment of anterior reference surface 146, FIG. 13, and distal reference surface 162 as a first and second locating datum for a chamfer speed block 600, FIG. 13a, to perform the required multiple chamfer cuts on distal femur 132.

In operation, the adjustable sizer cut guide device, including the first readable scale, is assembled such that the sizer member, the femoral cutting guide and the slide stone are slidably interconnected. The slide stone is selected according to the valgus angle of the patient's anatomy. The slide stone receives the intramedullary rod which is inserted into the patient's intramedullary canal, and the adjustable sizer cut guide device is positioned in engagement with the distal and posterior surfaces of the distal end of the femur.

An adjustable referencing device, including the second readable scale, is removably attached to the adjustable sizer cut guide device. The adjustable sizer cut guide device and the adjustable referencing device are concurrently adjusted until the first readable scale and the second readable scale provide a matching reading which corresponds to an implant size. Metal pins are driven through openings in the adjustable sizer cut guide device so that the device is secured to the distal femur and positioned for desired size and rotation. The adjustable referencing device is removed from the adjustable sizer cut guide device. A saw blade of a surgical cutting instrument is inserted into the anterior reference cut guide slot which is provided in the femoral cutting guide, and the anterior femoral reference cut is formed in the anterior surface of the distal femur.

The distal cut guide is positioned against the surface of the anterior reference cut and temporarily attached to the femoral cutting guide with metal positioning pins. Metal pins are also driven through the zero reference holes in the distal cut guide and into the distal femur and the positioning pins are removed. The intramedullary rod is removed from the intramedullary canal and from the slide stone. The metal pins which secure the adjustable sizer cut guide device are removed from the distal femur and the adjustable sizer cut guide device is removed from its position on the distal femur. A saw blade of a surgical cutting instrument is inserted into the distal cut guide slot which is provided in the distal cut guide, and the distal femoral cut is formed in the distal surface of the distal femur. The metal pins securing the distal cut guide to the distal femur are removed and the distal cut guide is removed. The distal femur includes the anterior femoral reference cut and the distal femoral cut. A speed block, or the like, is positioned and secured on the distal femur in a known manner to provide for the anterior and posterior cuts to be made and to provide for the anterior and posterior chamfer cuts to be made.

Figure 14:
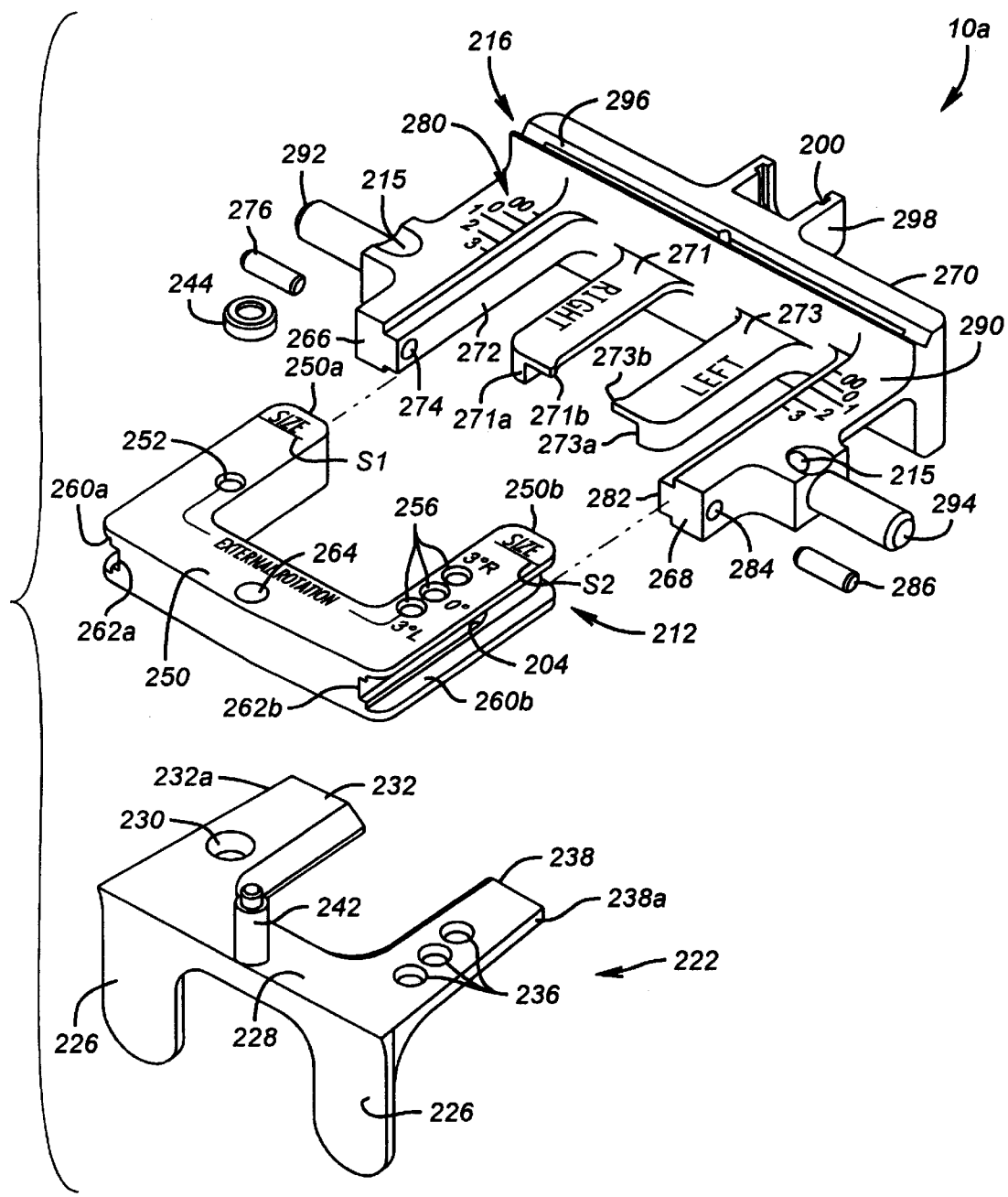
FIG. 14 is an exploded view illustrating another embodiment of a distal femur sizing and resecting device.
Figure 15:
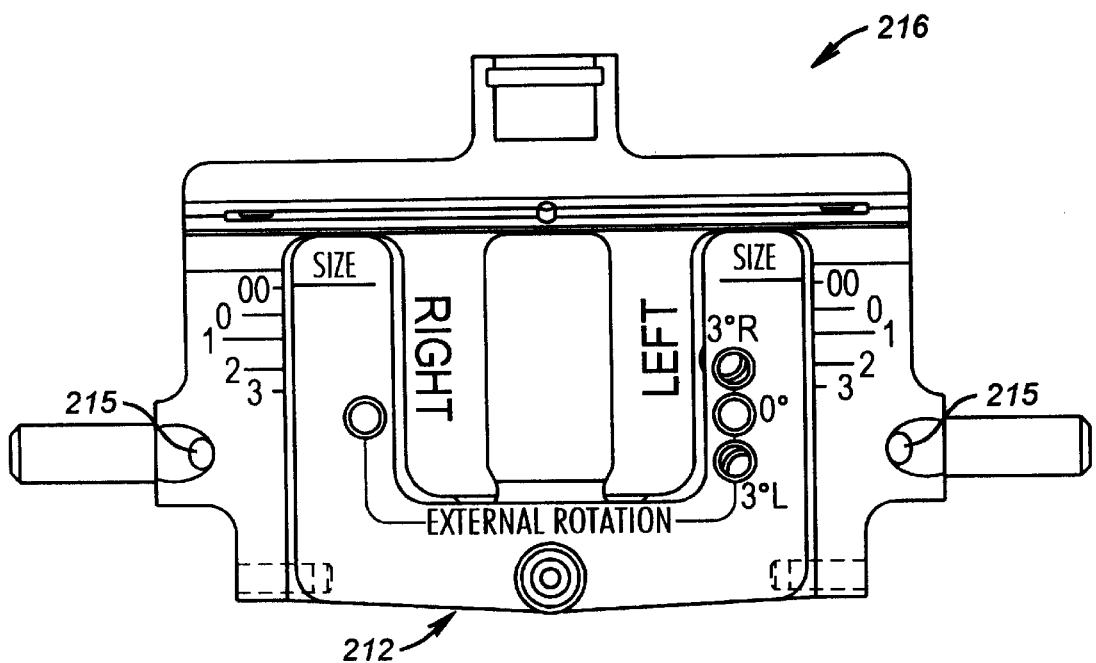
FIG. 15 is a top view illustrating an embodiment of assembled portions of the device of FIG. 14.
Figure 16:
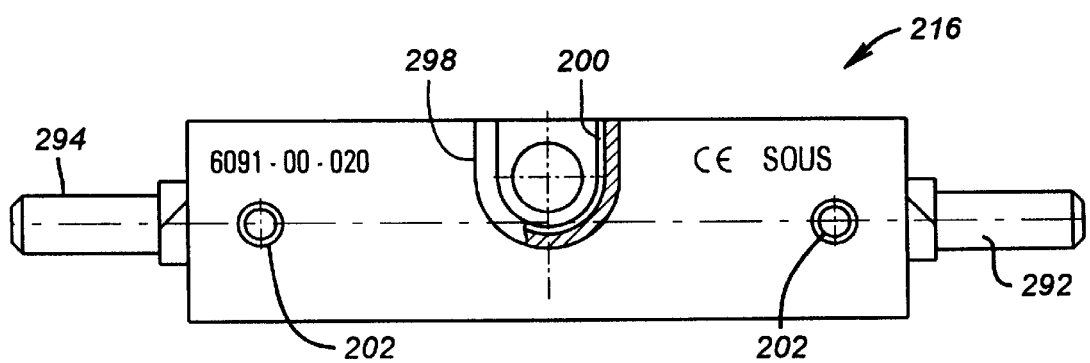
FIG. 16 is an end view illustrating an embodiment of the femoral cut guide of FIG. 14.

In another embodiment, FIGS. 14–16, a modified device 10a includes a platform 222, FIG. 14, which is generally L-shaped including a pair of paddles 226 and a bifurcated extension 228 including a flange 232 and a flange 238. A rotation aperture 230 is formed in flange 232. A plurality of rotation apertures 236 are formed in flange 238. A pivot pin 242 extends from platform 222.

Sizer member 212 is generally U-shaped including a bifurcated portion 250 having a first portion 250a including a size scale marker S1, and a second portion 250b including a size scale member S2. First portion 250a includes a rotation aperture 252. Second portion 250b includes a plurality of rotation apertures 256. Sizer member 212 also includes a pair of opposed external grooves 260a and 260b, and a pair of opposed pin grooves 262a and 262b formed in external grooves 260a and 260b, respectively. A shoulder button 244 is engageable with pivot pin 242 which extends through an aperture 264 formed in sizer member 212.

When assembled, pivot pin 242 extends through aperture 264 and receives shoulder button 244. A tapered edge 232a of flange 232 and a tapered edge 238a of flange 238 permit pivotal movement between sizer member 212 and platform 222. Also, such pivotal movement permits flange 232 to move relative to first portion 250a and simultaneously permits flange 238 to move relative to second portion 250b. This permits alignment between rotation apertures 230 and 252, and alignment between rotation apertures 236 and 256.

Femoral cut guide 216, is generally U-shaped including a first sizer extension 266, a second sizer extension 268 and a flange 270. First sizer extension 266 includes an internal tongue 272, an aperture 274 for receiving a pin 276 to protrude therefrom, and a readable size index 280, including indices of 00, 0, 1, 2 and 3 for alignment with size scale marker S1. Second sizer extension 268 includes an internal tongue 282, opposite tongue 272, an aperture 284 for receiving a pin 286 to protrude therefrom, and a readable size index 290, including indices of 00, 0, 1, 2 and 3 for alignment with size scale marker S2. Also, a pair of extensions 292 and 294 extend in opposite directions from extensions 266 and 268, respectively. Flange 270 includes a femoral cut guide slot 296, a first femoral receiver 298 including a groove 200 formed therein, and a second femoral receiver including a pair of femoral temporary pin apertures 202, see FIG. 16. When assembled, FIGS. 14 and 15, tongues 272 and 282 slide within grooves 260a and 260b, respectively. Pins 276 and 286 slide within grooves 262a and 262b, respectively, and capture sizer member 212 for limited sliding motion with femoral cut guide 216 by means of a stop 204, only one of which is visible in FIG. 14. A pair of slide stone retainer guides 271 and 273 extend from flange 270. Guide 271 includes a slot 271a and a stop 271b. Similarly, guide 273 includes a slot 273a and a stop 273b. Angled openings 215 are available to receive pins if it is desired to create a macro-lock.

Figure 17:
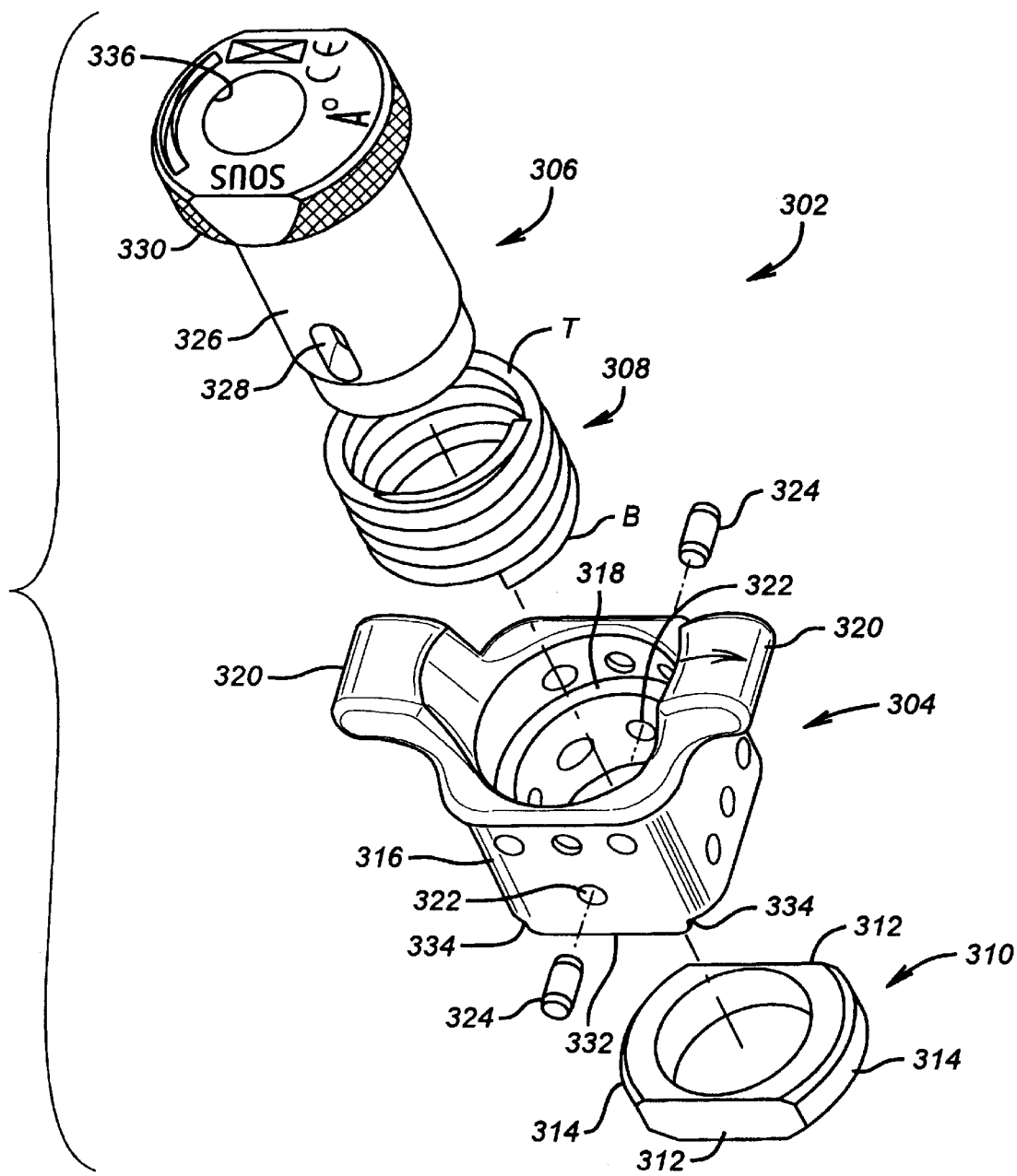
FIG. 17 is an exploded view illustrating another embodiment of a slide stone.
Figure 18:
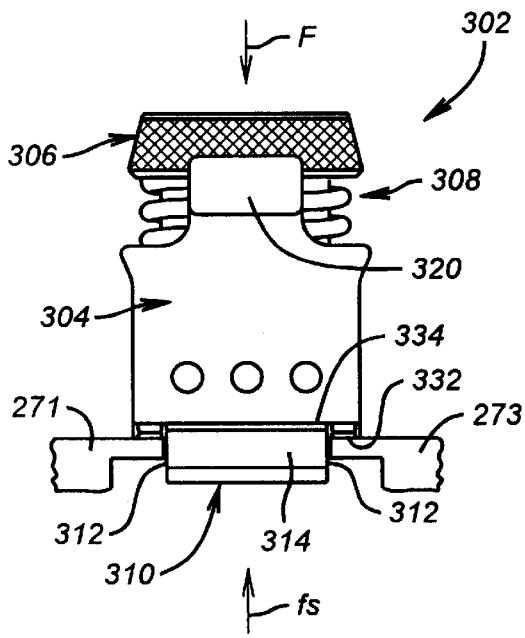
FIG. 18 is a side view of the slide stone of FIG. 17.
Figure 19:
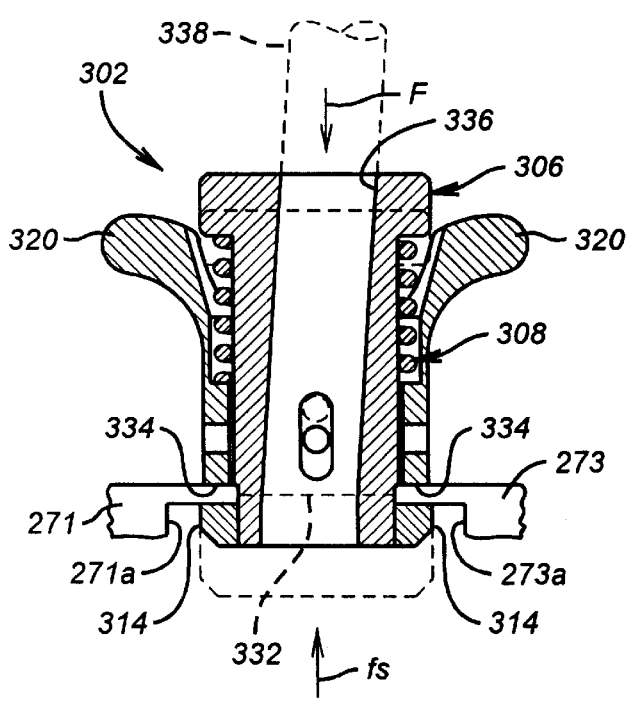
FIG. 19 is a cross-sectional side view of the slide stone of FIG. 17.

A slide stone 302, FIGS. 17–19, includes a carriage member 304, a plunger 306, a compression spring 308, and a cap 310 including a pair of opposed flats 312 and, a pair of opposed tongues 314. Carriage member 304 includes a tubular body 316, having a spring seat 318 formed therein and a pair of opposed winglets 320 extending therefrom. A pair of opposed pin holes 322 are provided through tubular body 316 for retaining a fixed pair of pins 324. Plunger 306 includes a cylindrical body 326 inserted through tubular body 316. A pair of opposed slots 328 receive pins 324 to guide reciprocal movement of plunger 306 in carriage 304.

A flange 330 at one end of plunger 306, seats an end T of spring 308. Spring seat 318 of carriage 304 seats an opposite end B of spring 308. Opposed tongues 314 of cap 310 are secured on an end of plunger 306 opposite flange 330. In this manner, plunger 306 is reciprocally movable in carriage member 304. Spring 308 urges tongue members 314 toward carriage member 304. A manual force, explained below, urges tongue members 314 away from carriage member 304 against a spring force so as to create a gap between cap 310 and an end 332 of carriage member 304. End 332 includes a pair of opposed locking slots 334. In this manner, tongue members 314 may be engaged with slots 271a and 273a, see also FIG. 14, of retainer guides 271 and 273, respectively. An angled aperture 336, formed in plunger 306, is provided for receiving an intramedullary rod 338.

Figure 18A:
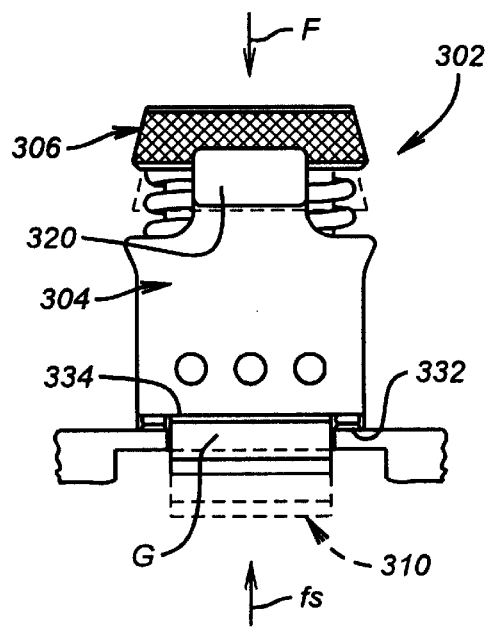
FIG. 18a is another side view of the slide stone of FIG. 17.

More specifically, slide stone 302, FIG. 18, is seated on retainer guides 271 and 273 by inserting opposed flats 312 between retainer guides 271 and 273 so that end 332 is seated on the retainer guides 271 and 273. A manual force F exerted on plunger 306 urges plunger 306 against a force fs of spring 308 so as to create a gap G, FIG. 18a, between cap 310 and end 332 of carriage member 304. This permits slide stone 302 to be rotated 90E, FIG. 19, so that slots 334 seat on retainer guides 271 and 273, and end 332 seats between retainer guides 271 and 273 to form a rotation lock. A release of force F on plunger 306 permits force fs of spring 308 to urge tongue members 314 into seated sliding engagement with slots 271a and 273a of retainer guides 271 and 273, respectively. Stops 271b and 273b, FIG. 14, limit sliding movement of slide stone 302 on retainer guides 271 and 273.

Figure 20:
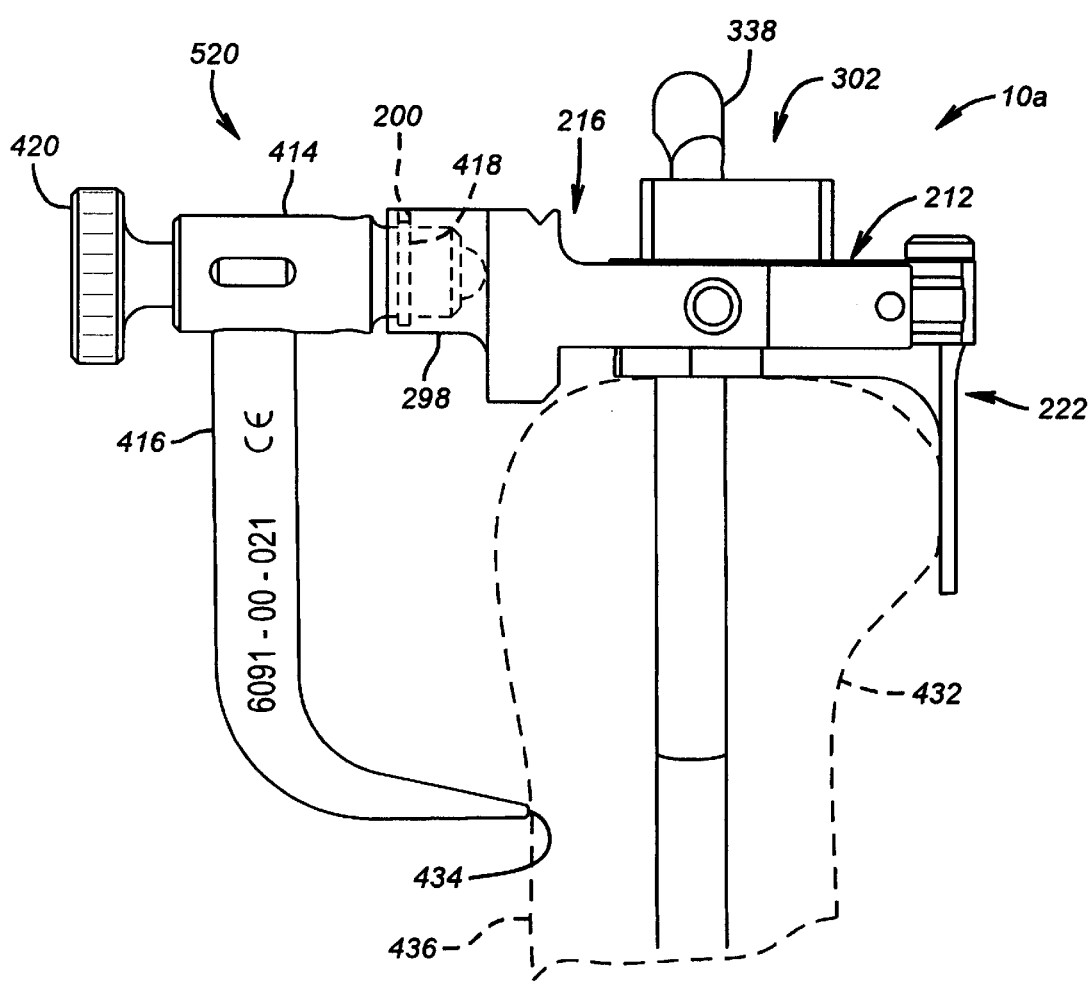
FIG. 20 is a side view illustrating an embodiment of assembled portions of the device engaged with a distal femur.

A modified reference device 520 includes a stylus holder 414 and a non-adjustable, single posterior referencing stylus 416, FIG. 20, rotatably mounted in receiver 298. The purpose of rotation is to allow the surgeon to place the tip 434 of the stylus 416, at a preferred location at the various contours of the anterior cortex 436 of the femur 432.

A tongue portion 418, on stylus holder 414 is inserted in grove 200. Rotation of threaded adjustable retainer 420, mounted on stylus holder 414, advances retainer 420 toward receiver 298, thus forcibly securing tongue 418 in groove 200. The distal cut guide 18, FIG. 10, can be used with the modified femoral cut guide 216, FIG. 14, as described above with reference to femoral cut guide 16.

In the embodiments of FIGS. 7 and 7b, described above, the surgeon balances cuts between the anterior and posterior dimensions of the bone to prevent notching of the anterior cortex. In the modified embodiments of FIGS. 14–20, the combination of the device 10a for distal femur sizing and resection, and the chamfer speed block 600, FIG. 13a, discussed above, provide a less exacting fit using a method wherein the surgeon picks a reference on the anterior cortex, either above or below an exact size for a nominal implant. The surgeon then makes a choice to use a larger or smaller chamfer speed block.

Figure 13A:
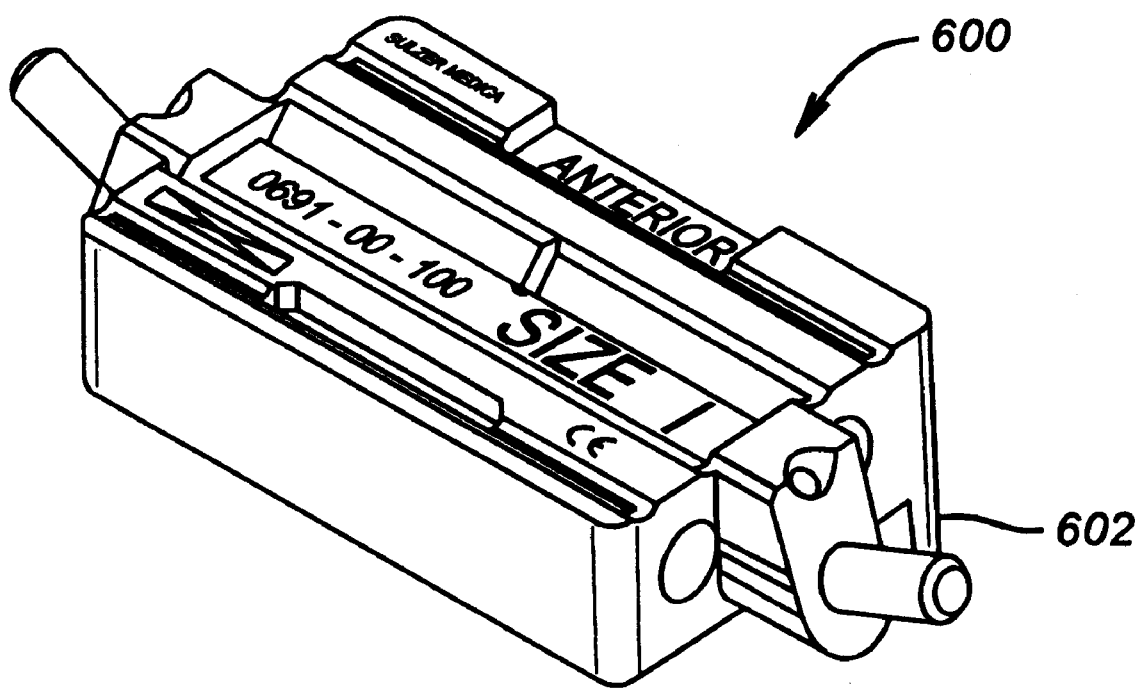
FIG. 13a is an isometric view illustrating an embodiment of a chamfer speed block.

If measurements on the femoral cut guide 216, FIG. 14, are between sizes on indices 280 and 290, then using the chamfer speed block, 600, FIG. 13a with an anterior reference ledge 602, the surgeon can choose to use a larger or smaller speed block to make appropriate cuts to best fit the patients anatomy or flexion requirements. Using a larger block will result in removing less bone from the posterior condyles which could be advantageous in patients with severe condyle erosion. Using a smaller block will result in removing more bone which could be advantageous in patients requiring more flexion.

As a result, one embodiment provides an apparatus for distal femur sizing and resection including a sizer member. An anterior femoral cut guide is movably engaged with the sizer member. Retaining guides extend from the femoral cut guide and a slide member is movably mounted on the retaining guides. A first member and a second member are sequentially removably attachable to the femoral cut guide. The first member is a reference device attached to the femoral cut guide for referencing, and the second member is a distal cut guide attachable to the femoral cut guide subsequent to removal of the reference device, to position the distal cut guide on the femur.

Another embodiment provides a distal femur cut guide including a sizer member and a platform pivotably connected to the sizer member. An anterior femoral cut guide is movably engaged with the sizer member and includes a first retainer for retaining a removable reference device for referencing, and a second retainer for retaining a removable distal cut guide subsequent to removal of the reference device, to position the distal cut guide on the femur. Retaining guides extend from the femoral cut guide, and a slide member is movably mounted on the retaining guides.

A further embodiment provides a carriage member included in the slide member. A plunger is resiliently mounted in the carriage member. The plunger is movable for retaining the slide member on the retaining guides.

As it can be seen, the principal advantages of these embodiments are that the device and the use thereof consolidate several time consuming steps into a compact procedure utilizing a multi-purpose instrument, to accurately locate and make the anterior femoral reference cut and the distal femoral reference cut.

Although illustrative embodiments have been shown and described, a wide range of modifications, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:
1. Apparatus for distal femur sizing and resection comprising:
a sizer member;
an anterior femoral cut guide movably engaged with the sizer member;
retaining guides extending from the femoral cut guide;
a slide member movably mounted on the retaining guides; and
a first member and a second member sequentially removably attachable to the femoral cut guide, the first member being a reference device attached to the femoral cut guide for referencing, and the second member being a distal cut guide attachable to the femoral cut guide subsequent to removal of the reference device, to position the distal cut guide on the femur.

2. The apparatus as defined in claim 1 further comprising a platform pivotably connected to the sizer member.

3. The apparatus as defined in claim 2 wherein the platform is L-shaped and includes a pair of paddles and a pair of flanges.

4. The apparatus as defined in claim 3 wherein the pair of flanges each have a tapered edge.

5. The apparatus as defined in claim 1 wherein each of the retaining guides includes a slot formed therein.

6. The apparatus as defined in claim 1 wherein each of the retaining guides includes a stop.

7. The apparatus as defined in claim 1 wherein each of the retaining guides includes a slot formed therein and also includes a stop at a terminal end thereof.

8. The apparatus as defined in claim 7 wherein the slide member includes a carriage member and a plunger resiliently seated in the carriage member.

9. The apparatus as defined in claim 8 wherein the plunger includes opposed tongues extending therefrom.

10. The apparatus as defined in claim 9 wherein the tongues are resiliently urged toward the carriage member.

11. The apparatus as defined in claim 8 wherein the plunger includes opposed tongues resiliently urged into the slots.

12. The apparatus as defined in claim 8 wherein carriage member includes an end engageable with the retaining guides to form a rotation lock.

13. The apparatus as defined in claim 9 wherein the carriage and plunger are rotatable between the retaining guides for engaging the opposed tongues in the slots.

14. The apparatus as defined in claim 1 wherein the sizer member includes a pair of slots formed therein and the femoral cut guide includes a pair of tongues engaged with the slots of the sizer member.

15. The apparatus as defined in claim 1 wherein the sizer member is U-shaped including first and second portions defining a gap therebetween, the retaining guides extending into the gap.

16. The apparatus as defined in claim 15 wherein the femoral cut guide is U-shaped including a pair of extensions, the first and second portions of the sizer member slidingly engaging the extensions of the femoral cut guide.

17. The apparatus as defined in claim 16 wherein the retaining guides are substantially parallel.

18. The apparatus as defined in claim 17 wherein the retaining guides include slots for guiding movement of the slide member and stops for limiting movement of the slide member.

19. An orthopedic sizing cut guide comprising:

a sizer member;

a platform pivotably connected to the sizer member;

an anterior femoral cut guide movably engaged with the sizer member and including a first receiver for a removable reference device for referencing, and a second receiver for positioning a distal cut guide on the femoral cut guide;

retaining guides extending from the femoral cut guide;

a slide member movably mounted on the retaining guides, the slide member including a carriage member; and a plunger resiliently mounted in the carriage member, the plunger being movable for retaining the slide member on the retaining guides.

* * * * *